(12) United States Patent
Roehrig et al.

(10) Patent No.: US 7,054,473 B1
(45) Date of Patent: May 30, 2006

(54) METHOD AND APPARATUS FOR AN IMPROVED COMPUTER AIDED DIAGNOSIS SYSTEM

(75) Inventors: Jimmy Roehrig, Palo Alto, CA (US); Sandra J. Stapleton, Palo Alto, CA (US); Julian Marshall, Los Altos, CA (US); Susan A. Wood, Mountain View, CA (US)

(73) Assignee: R2 Technology, Inc., Sunnyvale, CA (US)

( * ) Notice: Subject to any disclaimer, the term of this patent is extended or adjusted under 35 U.S.C. 154(b) by 817 days.

(21) Appl. No.: 09/992,059

(22) Filed: Nov. 21, 2001

(51) Int. Cl.
*G06K 9/00* (2006.01)

(52) U.S. Cl. .......... 382/128; 382/274; 378/37

(58) Field of Classification Search ........ 382/128–133, 382/156, 162, 169, 172, 194, 196, 203, 209, 382/232, 237, 240, 243, 248, 260, 268–295, 382/302; 600/408, 409; 378/37, 28; 707/102; 356/443; 250/453.11
See application file for complete search history.

(56) References Cited

U.S. PATENT DOCUMENTS

| | | | |
|---|---|---|---|
| 4,907,156 A | 3/1990 | Doi et al. | |
| 4,983,044 A | 1/1991 | Schweber | |
| 5,133,020 A | 7/1992 | Giger et al. | |
| 5,289,374 A | 2/1994 | Doi et al. | |
| 5,343,390 A | 8/1994 | Doi et al. | |
| 5,452,367 A | 9/1995 | Bick et al. | |
| 5,491,627 A | 2/1996 | Zhang et al. | |
| 5,537,485 A | 7/1996 | Nishikawa et al. | |
| 5,586,160 A * | 12/1996 | Mascio | 378/37 |
| 5,657,362 A | 8/1997 | Giger et al. | |
| 5,790,690 A * | 8/1998 | Doi et al. | 382/128 |
| 5,799,100 A | 8/1998 | Clarke et al. | |
| 5,828,774 A | 10/1998 | Wang | |
| 5,873,824 A * | 2/1999 | Doi et al. | 600/408 |
| 5,881,124 A | 3/1999 | Giger et al. | |
| 6,198,838 B1 | 3/2001 | Roehrig et al. | |
| 6,263,092 B1 | 7/2001 | Roehrig et al. | |
| 6,434,262 B1 * | 8/2002 | Wang | 382/132 |
| 6,483,933 B1 | 11/2002 | Shi et al. | |
| 6,516,045 B1 | 2/2003 | Shepard et al. | |
| 6,580,818 B1 * | 6/2003 | Karssemeijer et al. | 382/128 |
| 6,584,216 B1 * | 6/2003 | Nyul et al. | 382/131 |
| 6,725,231 B1 * | 4/2004 | Hu et al. | 707/102 |
| 6,738,500 B1 * | 5/2004 | Bankman et al. | 382/128 |
| 2002/0070970 A1 | 6/2002 | Wood et al. | |
| 2003/0095697 A1 | 5/2003 | Wood et al. | |

OTHER PUBLICATIONS

U.S. Appl. No. 10/079,327 filed Feb. 19, 2002, inventor Jimmy Roehrig.
U.S. Appl. No. 09/721,347 filed Nov. 22, 2000, inventor Harmann et al.

(Continued)

*Primary Examiner*—Daniel Miriam
*Assistant Examiner*—Seyed Azarian
(74) *Attorney, Agent, or Firm*—Blakely, Sokoloff, Taylor & Zafman LLP; Judith A. Szepesi

(57) ABSTRACT

A method and apparatus for analyzing a medical image obtained from one of a plurality of modalities, the method comprising normalizing the medical image to create a uniform display quality regardless of the original modality of the image.

31 Claims, 16 Drawing Sheets

OTHER PUBLICATIONS

Jain, Anik K., et al., "Algorithms Clustering Data," Pretice Hall, Mar. 1998.

Kupinski, Matt, et al., "Computerized detection of mamographic lesions: Performance of artificial neural network with enhanced feature extraction," SPIE vol. 2434, p. 598.

Giger, Maryellen, et al., "Image Processing and Computer-aided Diagnosis," Radiol Clin North Am, May 1996, vol. 34, N 3, pp. 565-596.

Burhenne, Linda J. Warren, et al., "Potential Contribution of Computer-aided Detection to the Sensitivity of Screening Mammography," Radiology, May 2000, pp. 554-562.

Giger, Maryellen, et al., "An 'Intelligent' Workstation for Computer-aided Diagnosis," RadioGraphics, May 1993, vol. 13, pp. 647-656.

Giger, Maryellen, et al., "Development of A "smart"workstation for use in mammography," In Proceedings of SPIE, vol. 1445, 1991, pp. 101-103.

Barski, Lori L., et al., "New automatic tone scale method for computed radiography," Proc SPIE, 1998, vol. 3335, pp. 164-178.

Roehrig, Jimmy, et al., "The promise of computer aided detection in digital mammography," European Jour of Radiology, vol. 31, 1997, pp. 35-39.

* cited by examiner a b

METHOD AND APPARATUS FOR AN IMPROVED COMPUTER AIDED DIAGNOSIS SYSTEM

FIELD OF THE INVENTION

The present invention relates to computer-aided diagnosis, and more specifically, to an integrated system for digital computer aided diagnosis for medical use.

BACKGROUND

Various systems and methods are currently known for computerized detection of abnormalities in radiographic images, such as those disclosed by Giger et al. in Radio-Graphics, May 1993, pp. 647–656; Giger et al. in Proceedings of SPIE, Vol. 1445 (1991), pp. 101–103; U.S. Pat. No. 4,907,156 to Doi et al.; U.S. Pat. No. 5,133,020 to Giger et al.; U.S. Pat. No. 5,343,390 to Doi et al.; U.S. Pat. No. 5,491,627 to Zhang et al. These systems are generally referred to as Computer-Aided Diagnosis systems, Computer-Aided Detection systems, or simply, CAD systems. Such systems are believed to be particularly useful to radiologists and other medical specialists in diagnostic processes and specifically in radiological screening procedures.

In a radiological screening procedure, such as screening mammography, true abnormalities such as cancers are believed to occur at a typical rate of about one case per one hundred patient examinations. It is believed a CAD system, serving as an electronic reminder or second reader, can assist radiologists in obtaining higher detection rates, or higher sensitivity for abnormalities. Additionally, such CAD systems can assist radiologists in reducing the misdiagnosis rate, or lowering the false negative rate. Thus, it is believed that the use of such CAD systems will continue to increase.

Since such CAD systems typically operate on medical images in high-resolution digital format, film-based medical images ordinarily must be scanned by a high-resolution scanner to convert the image data into digital form. As systems change, the digital image acquisition devices cannot be interfaced with such CAD systems. Additionally, in a practice covering multiple areas, for example mammograms as well as CT scans, multiple such analysis devices must be used, one for each modality. This is wasteful, and reduces the use of such CAD systems.

SUMMARY OF THE INVENTION

A method and apparatus for analyzing a medical image obtained from one of a plurality of modalities, the method comprising normalizing the medical image to create a uniform display quality regardless of the original modality of the image.

BRIEF DESCRIPTION OF THE DRAWINGS

The present invention is illustrated by way of example, and not by way of limitation, in the figures of the accompanying drawings and in which like reference numerals refer to similar elements and in which:

FIG. 10 is a data flow illustrating the various steps taken for a CT scan.

DETAILED DESCRIPTION

A method and apparatus for an integrated computer aided diagnosis system is described. The computer aided diagnosis system may take as input analog (film/screen) or direct digital medical images such as mammograms, chest X-rays, CT scans, etc. The system is designed to improve the convenience, accuracy, productivity, and peace of mind associated with the medical personnel's viewing process.

The system uses established communication standards for inputting medical images, and is able to handle various input sources, including films/screens of various types, and digital inputs of various resolutions. Furthermore, the system may be able to work with two as well as three-dimensional inputs. The system also uses established communication standards to output the CAD results with adequate information to display CAD information in an optimized way. For another embodiment, a proprietary communication method may be used to input medical images and/or output results.

An automated preprocessing algorithm is used for orienting, identifying, and preparing images from multiple sources to be analyzed. An example of such an algorithm is described in a patent application by Hartmann et al.: U.S. patent application Ser. No. 09/721,347. The system further exploits the information provided by the computer aided diagnosis (CAD) system to display an improved visualization of the image, showing suspicious regions where they might otherwise be hard to visualize—a CAD-driven display.

The system also has the flexibility of being "upgraded" over time as new inputs and outputs become available for different input types and different disease types. Due to this increased flexibility, the user will also enjoy a degree of protection from obsolescence while the radiology department is transitioning from film based to digital based. The same processor that performs CAD on film images presently, can, due to the normalization process described below, accept or be easily upgraded to input and output using a digital system.

Figure 1:
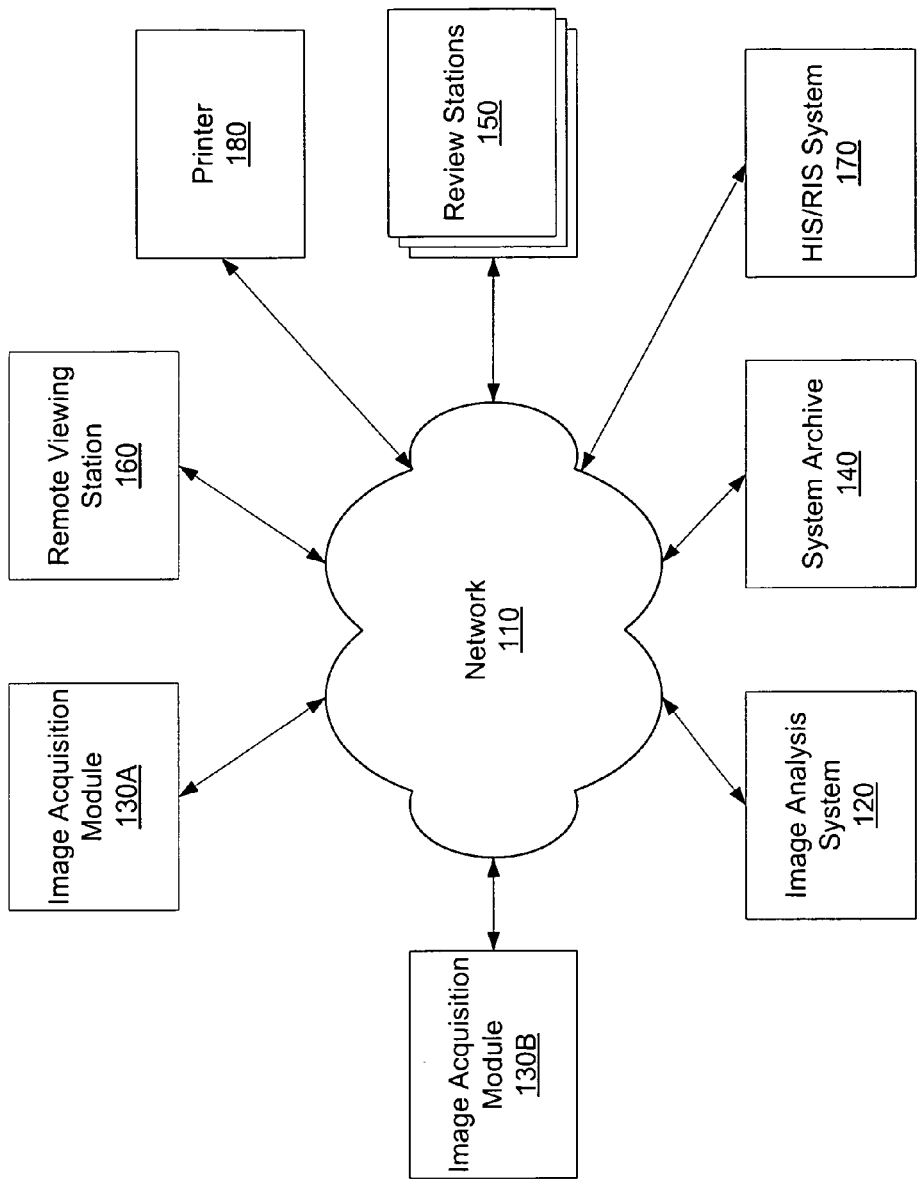
FIG. 1 is a block diagram of a network that may be used with the present invention.

FIG. 1 is a block diagram of a network that may be used with the present invention. The system includes one or more image acquisition modules 130A, 130B. The image acquisition modules may be conventional film image acquisition systems, which are known in the art, and/or digital image acquisition systems. Standard methods may be used to obtain the analog or digital images, whether two or three-dimensional. The outputs of the image acquisition modules 130A, 130B, are digital or analog images. One example of a film based image acquisition system 130A is described in Wang, U.S. Pat. No. 5,828,774.

These images are passed to image analysis system 120. For one embodiment, the images are sent through network 110 to image analysis system 120. Network 110 may be an internal local area network (LAN), a wide area network (WAN), the Internet, or any other type of network. For one embodiment, if the network 110 is not a local internal network, then the images sent by image acquisition modules 130A, 130B are encrypted or in some other way protected to ensure the patient's privacy. This permits the use of a centralized image analysis system 120 which may receive images from multiple offices that may be located anywhere in the world. Similarly, the analyzed images/output may be sent to review stations anywhere in the world.

The image analysis system 120 performs the preprocessing, recognition, and/or post-processing of the images. The image analysis system 120 is described in more detail below.

The system, for one embodiment, further includes a HIS/RIS (hospital information system/radiology information system) system 170. The HIS/RIS system 170 is coupled to the image analysis system 120, either directly or through network 110. The HIS/RIS system 170 provides patient data, in one of a variety of formats. For one embodiment, the HIS/RIS system 170 may provide data in the HL7 format. Alternative formats may be used. The images processed by image analysis system 120 may be stored within a patient record, in the HL7 format. For another embodiment, the image may be stored in DICOM format, including the appropriate patient information.

For one embodiment, a copy of the processed images is stored in system archive 140, permitting retrieval of the image at a later time. For one embodiment, a lower resolution image is stored. For one embodiment, the stored image does not include any tagging or other indicators added by image analysis system 120. For another embodiment, the owner of the system may select the format of the images stored in system archive 140.

The images are displayed to a reviewer at review station 150. Review stations 140 may be directly coupled to image analysis system 120, or coupled through a network. For one embodiment, the images may further be viewed at remote viewing stations 160. Remote viewing stations 160 may be conventional computer systems coupled to the network 110, may be handheld devices, laptop computers, or any other display mechanism. The remote viewing stations 160 may be wirelessly linked to the network, to permit fully mobility. This permits a doctor in a remote location to review the images, and may be used to allow the patient or others to review the images remotely. Thus, for example, a radiologist at a central location may initially review and analyze the images, and annotate them. Then, the images, and notation—or a report generated based on the images and notation—is sent to a remote system where the doctor can review the data with the client.

For one embodiment, the images, report, or other output may be sent to a printer 180. The printer 180, for one embodiment, may print to film, to permit conventional review of the enhanced images. For one embodiment, the printer 180 may print multiple images, for example, one set of original images, a set of enhanced images, and a set of enhanced images with markers indicating the abnormalities found by the image analysis system 120. The printer 180 may be coupled to the image analysis system 120 and/or the system archive 140 either directly or through network 110. As discussed above with respect to the review stations 150, 160, the printer 180 need not be in the same location as the image analysis system 120.

Of course, not all of these elements must be present in order to implement the present system. At its simplest, the system includes an image acquisition module 130A, an image analysis system 120, and a review station 150 that permits viewing of the images. These systems 120, 130A, 150 may be coupled directly, without the use of a network 110. At its most complex, the system may be a distributed system having image acquisition modules 130A, 130B at various remote locations, while a central archive 140 and one or more image analysis systems 120 are used to process the acquired images. Then, the images may be sent to various local or remote review stations 150, 160. Note that although the image analysis system 120 illustrated as once central device, it may be a distributed system.

Figure 2:
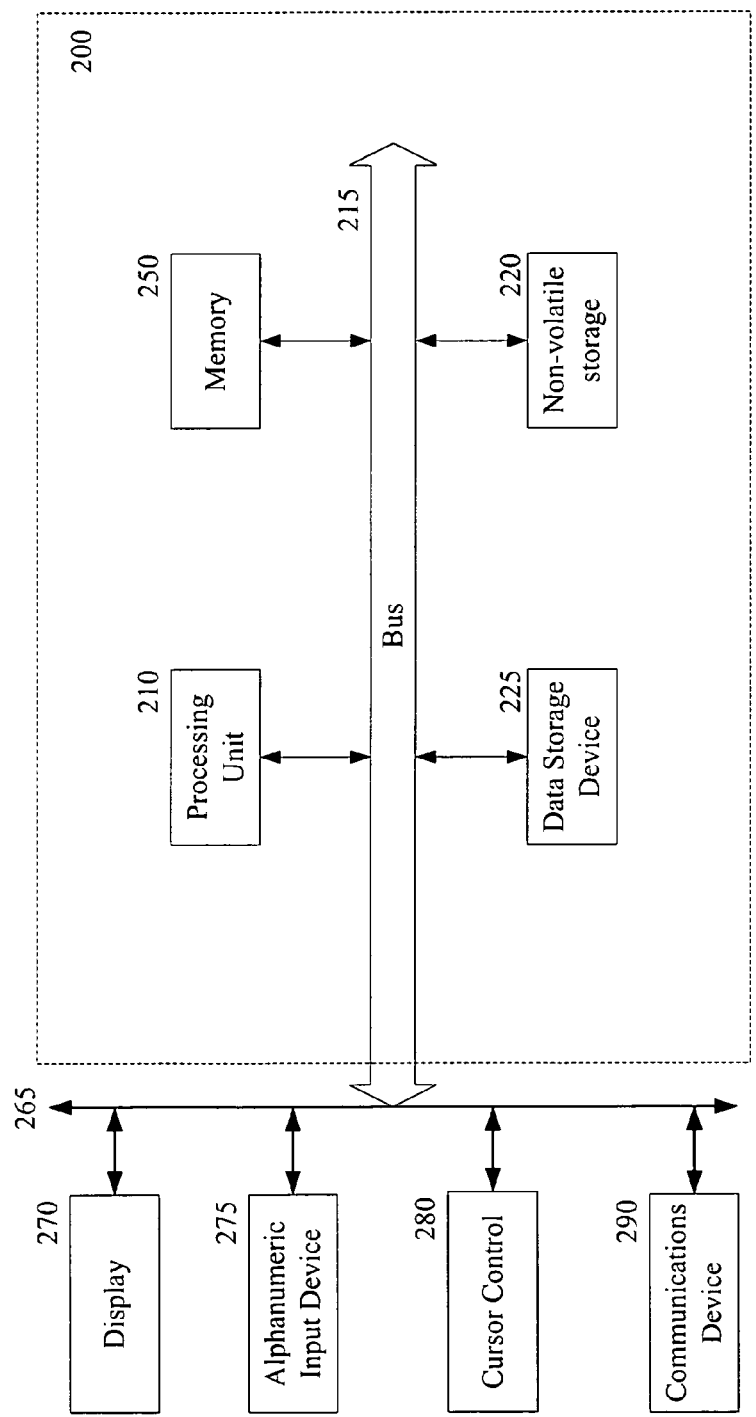
FIG. 2 is a block diagram of a computer system that may be used with the present invention.

FIG. 2 is one embodiment of a computer system that may be used with the present invention. It will be apparent to those of ordinary skill in the art, however that other alternative systems of various system architectures may also be used.

The data processing system illustrated in FIG. 2 includes a bus or other internal communication means 215 for communicating information, and a processor 210 coupled to the bus 215 for processing information. The system further comprises a random access memory (RAM) or other volatile storage device 250 (referred to as memory), coupled to bus 215 for storing information and instructions to be executed by processor 210. Main memory 250 also may be used for storing temporary variables or other intermediate information during execution of instructions by processor 210. The system also comprises a read only memory (ROM) and/or static storage device 220 coupled to bus 215 for storing static information and instructions for processor 210, and a data storage device 225 such as a magnetic disk or optical disk and its corresponding disk drive. Data storage device 225 is coupled to bus 215 for storing information and instructions.

The system may further be coupled to a display device 270, such as a cathode ray tube (CRT) or a liquid crystal display (LCD) coupled to bus 215 through bus 265 for displaying information to a computer user. An alphanumeric input device 275, including alphanumeric and other keys, may also be coupled to bus 215 through bus 265 for communicating information and command selections to processor 210. An additional user input device is cursor control device 280, such as a mouse, a trackball, stylus, or cursor direction keys coupled to bus 215 through bus 265 for communicating direction information and command selections to processor 210, and for controlling cursor movement on display device 270.

Another device, which may optionally be coupled to computer system 200, is a communication device 290 for accessing other nodes of a distributed system via a network. The communication device 290 may include any of a number of commercially available networking peripheral devices such as those used for coupling to an Ethernet, token ring, Internet, or wide area network. The communication device 290 may further be a null-modem connection, or any other mechanism that provides connectivity between the computer system 200 and the outside world. Note that any or all of the components of this system illustrated in FIG. 2 and associated hardware may be used in various embodiments of the present invention.

It will be appreciated by those of ordinary skill in the art that any configuration of the system may be used for various purposes according to the particular implementation. The control logic or software implementing the present invention can be stored in main memory 250, mass storage device 225, or other storage medium locally or remotely accessible to processor 210.

It will be apparent to those of ordinary skill in the art that the system, method, and process described herein can be implemented as software stored in main memory 250 or read only memory 220 and executed by processor 210. This control logic or software may also be resident on an article of manufacture comprising a computer readable medium having computer readable program code embodied therein and being readable by the mass storage device 225 and for causing the processor 210 to operate in accordance with the methods and teachings herein.

The present invention may also be embodied in a handheld or portable device containing a subset of the computer hardware components described above. For example, the handheld device may be configured to contain only the bus 215, the processor 210, and memory 250 and/or 225. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 210, a data storage device 225, a bus 215, and memory 250, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor 210. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, electrical, optical, acoustical or other forms of propagated signals (e.g. carrier waves, infrared signals, digital signals, etc.).

Figure 3A:
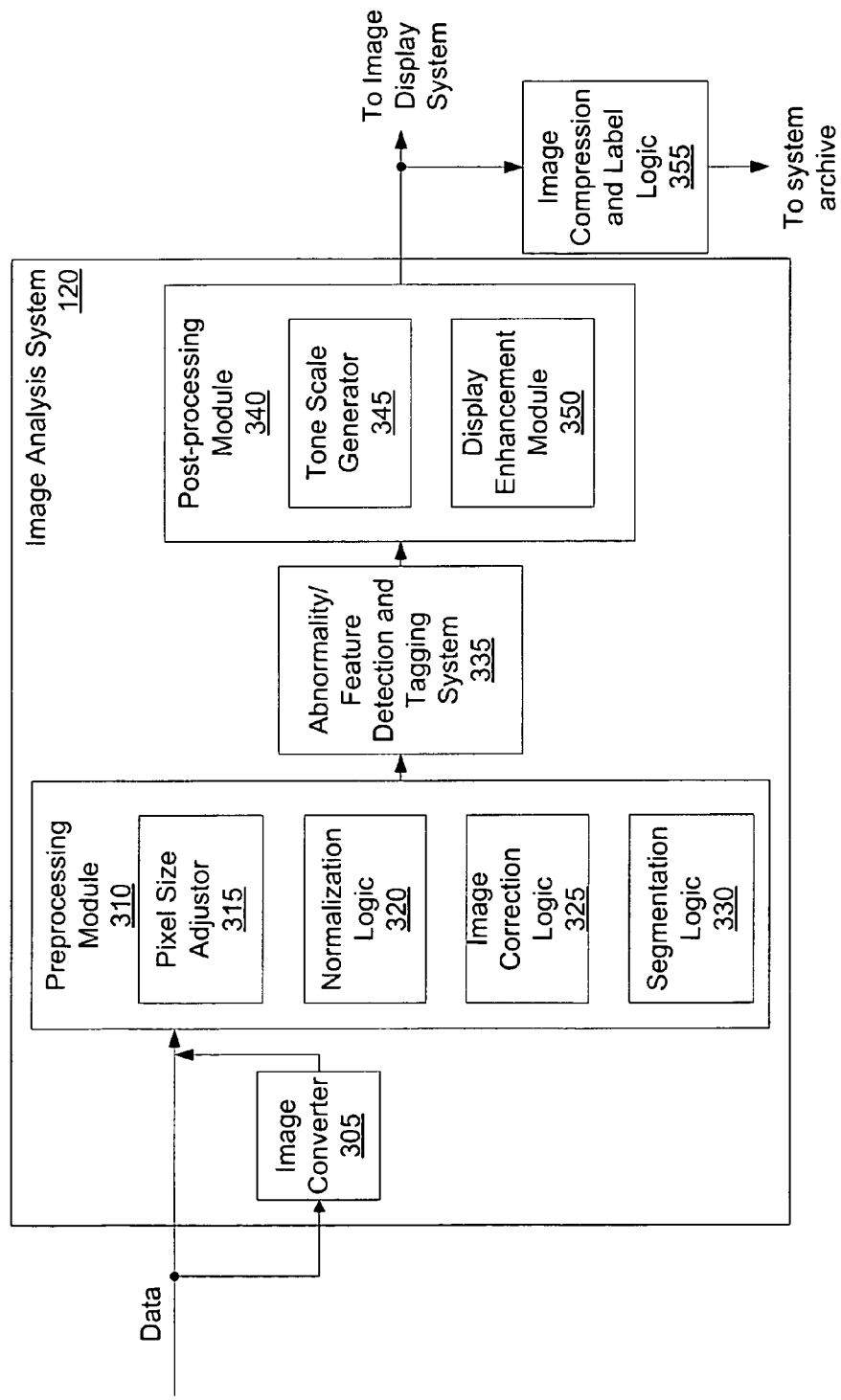
FIG. 3A is a block diagram of one embodiment of an image analysis system.

FIG. 3A is a block diagram of one embodiment of the inputs and outputs of the present computer aided diagnosis system (CADS). The system 120 receives data from image acquisition modules (not shown) in either digital or analog form. The system 120 may further receive historical data about the patient, including previous medical images, from the system archive. The system 120 may further receive other patient medical data. Furthermore, the system 120 may receive multiple elements of the same anatomical features, in two or three dimensions. Thus, for example, a mammography image may be further interpreted in view of an ultrasound, or another type of image.

The system 120 includes an image converter 305, which converts non-digital images to digital images. For one embodiment, the image converter 305 also converts the image into a standard format, such as DICOM, or General Electric's proprietary format HL7. For one embodiment, this includes adding patient information.

The system 120 includes a preprocessing module 310, which receives the digital image data from image acquisition modules. The pre-processing module 310 includes a pixel size adjustor. The pixel size adjustor 315 provides the ability to process images with a wide range of pixel sizes. For example, mammography images may be input with 50 micron pixels, 100 micron pixels, 86 micron, etc. The pixel size adjustor 315 is able to accept all sizes of inputs, and delivers a standardized output, having a preselected pixel size. The standardization performed by pixel size adjustor 315 is important for the abnormality detection, since the image resolution is identical for all input formats.

The algorithm used by the abnormality detection system 335 typically looks for abnormalities at well-defined scales, or sizes. For example, microcalcifications in mammograms are very small, often 100 to 250 microns in size. Digital filters with high sensitivity at those scales would be used to detect such microcalcifications. In contrast, masses are generally larger than 5 mm when visible. Thus, a different detection algorithm would be used to detect masses. Furthermore, the size of the abnormal object is an important parameter, and many algorithms incorporate the knowledge of size, and therefore pixel size into the analysis of the object.

An optimal pixel size, or "canonical" pixel size is usually chosen, that is appropriate to the type of image being analyzed, and the algorithms being used. When an image is input with a different pixel size, it is converted into the canonical size so the algorithm can operate correctly on it. If the input image is lager than the canonical size, this may be accomplished by subsampling or filtering down. If the input image is smaller, this can be accomplished by interpolating up to the larger size.

Using such pixel size adjusting is a useful component of a system that accepts images from different acquisition devices, such as film/screen, computed radiography, or digital acquisition devices.

The normalization and contrast equalization (NACE) logic 320 processes the images to generate gray-scale values that are indicative, as much as possible, of anatomy only. The NACE logic 320 processes the images to generate gray-scale values that are sensitive, as much as possible, to contrast changes due anatomy, rather than incidental variables such as x-ray technique, exposure, energy, etc. A substantial benefit of this operation is that CAD accuracy, i.e. sensitivity and specificity, is generally improved. This is because CAD ultimately attempts to separate abnormalities from normal structure by looking for physical variables (such as contrast) where the distribution of the variable values differs between normal and abnormal. In general, by eliminating incidental variables and allowing pixel gray values to better reflect real differences in anatomy, the distributions of these physical variables will become narrower, thus allowing better separation. Thus, the NACE logic 320 produces an output that is generally independent of acquisition technique, compression, mechanical idiosyncrasies, etc. The mechanics of implementing the NACE logic 320 is explained in more detail below.

The image correction logic 325 performs image correction appropriate to the anatomical features being analyzed. Thus, image correction may include correction for noise, correction for tilt, or other aspects of the image. For one embodiment, image correction logic 325 further performs a preliminary analysis on the quality of the image. If the image quality is not sufficient for feature detection, the system may request that a new image be taken. If the image analysis system 120 is on the same system as the image acquisition, this process may be performed immediately. In that instance, the notification that a new image should be taken may be very fast, taking only a few seconds. This is advantageous since it means that the patient is not required to return for a new image to be taken.

Segmentation logic 330 may be used to segment the various body parts. Segmentation is an operation that assigns all image pixels that share some trait in common to a single class. As an example, segmentation algorithms such as described in U.S. Pat. No. 5,452,367 by Bick et al.; may be used to find the skin line of the breast in FIGS. 8A and 8B, thus assigning all pixels inside the skin line to the "breast region," and all pixels outside to be in the background region. A further example that would be relevant in chest radiography is code that would segment the lung fields in a chest image, such as described by Bram Van Ginneken (Bram van Ginneken, Computer-Aided Diagnosis in Chest Radiography, Ph.D Thesis, Image Sciences Institute, University Medical Center Utrecht, Utrecht, Netherlands). Segmentation algorithms may be used to further segment the chest image into mediastinem, heart, diaphragm, ribs, etc. In other medical images, segmentation might be used to separate different organs in the image.

The normalized and segmented image is then passed to the abnormality and feature detection and tagging system 335. This module may use one or more of the existing systems designed for the purpose. Examples have been described, for example, in U.S. Pat. Nos. 6,263,092; 6,198,838; 5,289,374; 5,657,362; and 5,537,485.

For one embodiment, the findings or results, positive or negative in nature, from the abnormal detection system 335 are in the form of a two-dimensional annotation map or x-y coordinate information, of the locations of the CAD-detected abnormalities. This module 335 will output a data stream that may include one or more of the following: locations and sizes of lesions, classifications of lesions, correlations of lesions from one medical image to another or to other medical evidence such as pathology reports, descriptors of lesions, linear, area and volumetric measurements of lesions, information regarding the success and failure of each algorithm attempted, including whether or not processing was a success, and the list of evidence used in the processing. The output will contain the location or x-y coordinate of the detected region of interest, whether a centroid, outline, perimeter, circumscribed circle or other localization, and will contain information describing what was located, and may optionally describe how the region or finding correlates spatially, temporally, or otherwise to other findings or anatomic structures.

The post-processing module 340 further processes the image. For one embodiment, the image at this point may include the abnormality tags, or other indicators from feature detection system 335. For another embodiment, the post-processing module 340 may receive the images directly from the pre-processing module 310.

For one embodiment, the image is a processed image, the post-processing operations described in this section are not applied and the system is not able to exploit the wider latitude of digital to help optimize the display.

Tone scale generator 345 adjusts the tone scale of the image to optimize display. Tone scale is, broadly speaking, a mapping of incoming exposure to a visual display according to some criterion such as optimal image quality or acceptability. The incoming exposure may be X-ray exposure, magnetic resonance level exposure, or another type depending on the modality used for image acquisition. The tone scale generator 345 obtains a new tone scale based on the requirement of visualizing a suspicious region or feature that is in a part of the data in the (hard to visualize) non-linear region of the image.

Figure 8A:
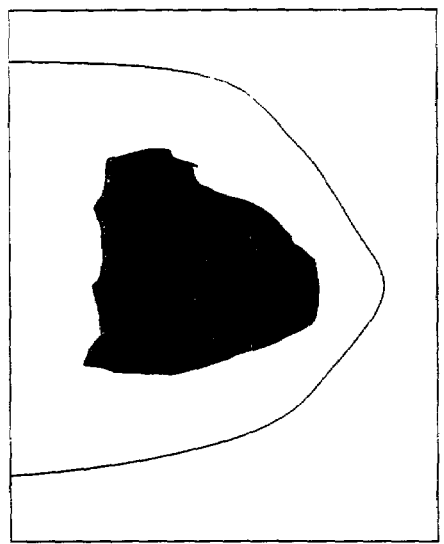
FIGS. 8A–E are examples of various images showing the effects of the processing.
Figure 8B:
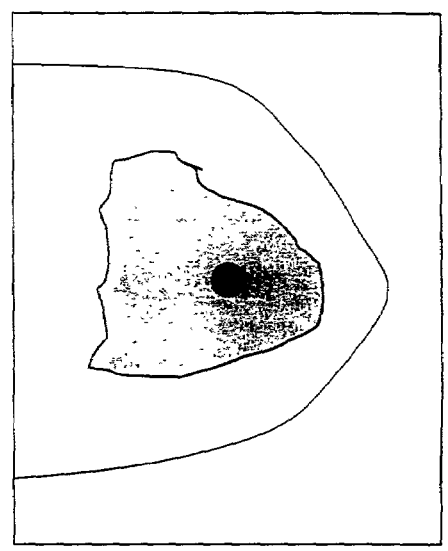

FIGS. 8A and B illustrate one example, in which the feature to be seen is in a dense portion of the anatomy, i.e. in the glandular region of the breast tissue. For mammograms, this hard-to-visualize region is typically found in dense parenchymal regions of the breast. The dense regions of chest radiographs, such as in the mediastinem, heart, or diaphragm, can be compensated for by the tone scale generator 345. Because these parts of the anatomy often fall into the non-linear regions of the tone scale, a suspicious feature, such as a nodule or lesion, will be difficult to see on the display device or film, because the contrast of the image will be very low in the region. On the other hand, it is necessary to limit the dynamic range of the image in some way, because all displays have limited dynamic range, whether they are films on light boxes or displays.

Figure 9A:
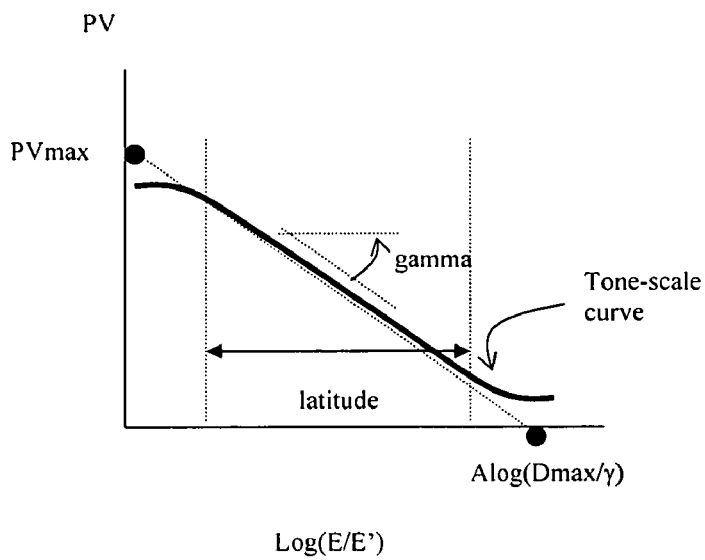
FIGS. 9A–H are exemplary curves illustrating the response of various inputs.

Tone scale is a mathematical mapping from the invisible physical signal (such as an X-ray transmittance) to the visible image signal. This is described, for example in L. Barsky et al., "New automatic tone scale method for computed radiography", Proc. SPIE, 3335, 164–178, 1998. The characteristic curve shown in FIG. 9A is typical of the tone scale mapping for diagnostic radiography. For diagnostic radiography, the compromise between visual contrast and dynamic range usually imposes serious constraints on the desirable tone scale. The optimal tone scale depends on the observer's interest, the characteristics of the display system, and the existence of an object that is important to see.

Because the dynamic range must be limited before display, it sometimes happens that the image "saturates" at dense parts of the anatomy, and equal contrast objects (physically) appear very low contrast visually, or disappear all together. Such regions may include the mediastinem, diaphragm, and heart region in the chest radiographs shown in FIG. 8E, or in the dense part of a mammogram shown in FIG. 8A.

The CAD algorithm does not require visualization to detect suspicious regions such as nodules. If the raw data from the digital detector is available, the computer algorithm is sensitive to density changes in dense regions before a tone scale (with its limitation on the dynamic range) is applied. If the CAD algorithm has found a region of interest, such as a nodule, in a region that would normally be difficult for the radiologist to visualize on a monitor or on film, the tone scale generator 345 creates a different tone scale such that that region can be visualized on the display.

For one embodiment, this modified tone-scale might be implemented as an optional feature in the user interface—such as a button that allows either the standard tone scale, or one of the modified tone scale. The button may allow the modified tone scale to be displayed when appropriate, or it could toggle between modified and original tone scale.

The display enhancement module 350 improves the quality of image being displayed. For one embodiment, this may include adjusting for display type, e.g. resolution and color depth, and other capabilities of the display.

The output of the post-processing module 340 is ready for display and/or storage. Of course, at this point, the output may be passed to another device or a separate system within the same device, for further processing and/or analysis. For one embodiment, the results of this analysis may be a processed image, markers indicating areas of abnormality, an image including the markers, a report listing the markers, or any combination of the above. For one embodiment, a high resolution processed image, not including the markers is output, along with a separate listing of the markers, either independently by location or in conjunction with an additional image. The additional image may be high resolution or low resolution.

For one embodiment, an image compression and label logic 355 may reformat the output for storage. For one embodiment, the stored data does not include the results of the abnormality/feature detection. Rather, only the corrected, normalized image is stored. For another embodiment, the full data set may be stored, or any subset of the data may be stored.

For one embodiment, the output will be produced in a standard format, such as DICOM Mammography CAD SR, to provide seamless interoperability with any manufacturer's workstations or display units that accept the standard formats. Furthermore, because the pre-processing module 310 and image converter 305 generate a "canonical image", the system may accept input from any type of system. Therefore, the image analysis system 120 may be integrated with any input and output sources, and may be inserted into a pre-existing system.

Figure 3B:
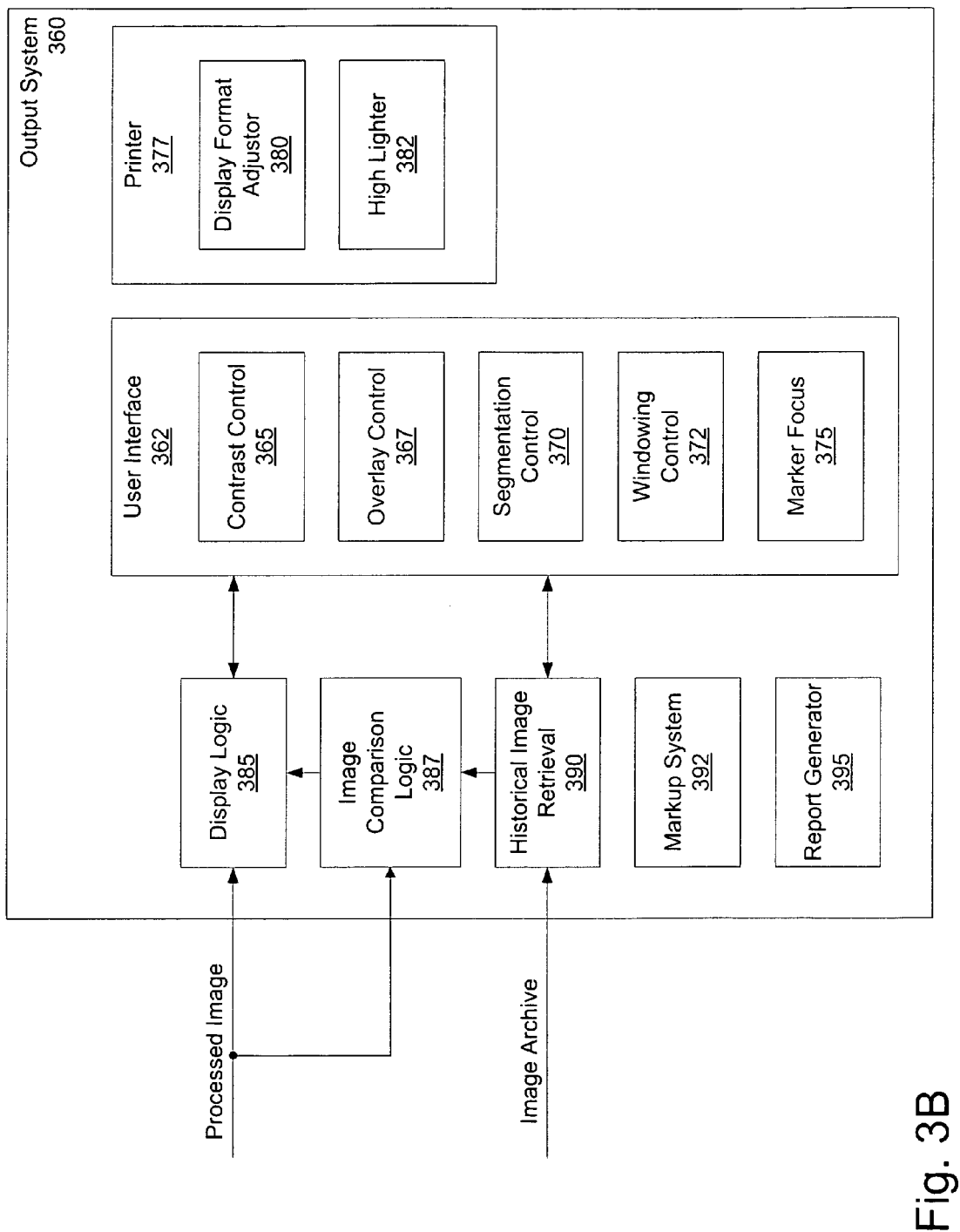
FIG. 3B is a block diagram of one embodiment of an output system for the image analysis system.

FIG. 3B is a block diagram of one embodiment of an output module for the image analysis system. The data may be received directly from the image analysis system 120, or from system archive, or through a network. The output system 360 may include a review station and/or a printer 377.

The display logic 385 is used to display the image, markers, reports, and other data to a reviewer. The display logic 385 may be controlled by user interface 362.

The display logic 385 may further display historical images, retrieved by historical image retrieval 390. As discussed above, images from previous years, as well as images taken with different devices/modalities may be used and shown to the reviewer. Historical image retrieval 390 may retrieve all of the data stored with respect to the patient, including images from past years, as well as images taken with different devices. The system may further include image comparison logic 387, which may compare the historical image/different device image with the current main image. The display may be a side-by-side display of the images, or a comparison, highlighting various aspects. As discussed above, the abnormality detection logic may also use the historical and other data for identifying abnormalities. Therefore, it is advantageous for the reviewer to be able to see the same data that the detection logic used.

User interface 362 includes controllers that permit a user to adjust contrast 365. This may be used by the radiologist or other medical personnel reviewing the image. The ability to adjust the contrast enables the reviewer to see objects in the darker portion of the image, by lightening only a portion of the image. For another embodiment, if multiple tone scales were generated—as discussed above—the reviewer may select from among those tone scales using contrast control 365.

The overlay control 367 permits the overlaying of the markers, identifying abnormalities detected, over an image. This may be useful if the display is a digital display, such that the reviewer may initially review the image without such indicators, and then may overlay the indications, to check the accuracy of the earlier detection.

Segmentation control 370 permits the subtraction of identified segmented elements of the image, or the change in tone/contrast of individual segments of the image.

Windowing control 372 generates a default window level setting. For one embodiment, this permits a system in which the reviewer never has to change the window level, regardless of the image size being reviewed, since the windowing control 372 automatically generates a window of the appropriate size. Additionally, for one embodiment, the reviewer may use the windowing control 372 to zoom in or out, or to generate a secondary window, displaying a particular region, selected by the reviewer.

The marker focus 375 permits marker based navigation. The marker based navigation may display the image, and call the user's attention to successive markers identifying abnormalities that were detected. For another embodiment, the marker based focus 375 provides an enlarged copy of the areas of interest, surrounding each of the markers. Thus, the user may invoke marker-based focus, and the jump from marker to marker on the image. This permits a careful review of each of the marked areas.

The system may further include a markup system 392, which permits the reviewer to add markings to the digital image. Furthermore, for one embodiment, the markup system 392 permits the reviewer to dictate notes that may be incorporated into a final report generated by report generator 395.

The output system 360 may further include a printer 377. For one embodiment, the printer 377 includes a display format adjustor 380. The display format adjustor 377 optimizes the format of the image and/or report for the printer 377 being used. The printer 377, for one embodiment, may print on film, to permit a reviewer to use the traditional light board to review the images.

The printer 377 may further include a highlighter 382, to highlight certain aspects of the data being printed. For example, the printer may print only a subset of the data, such as significant markers, or the data that was added by the reviewer using the markup system 392.

Note that output system 360 may be distributed over multiple devices, located in different locations. For example, the display logic 385 may be located separately from the user interface, image comparison, or printer. For another embodiment, all of these elements may be located on the same system.

Figure 4:
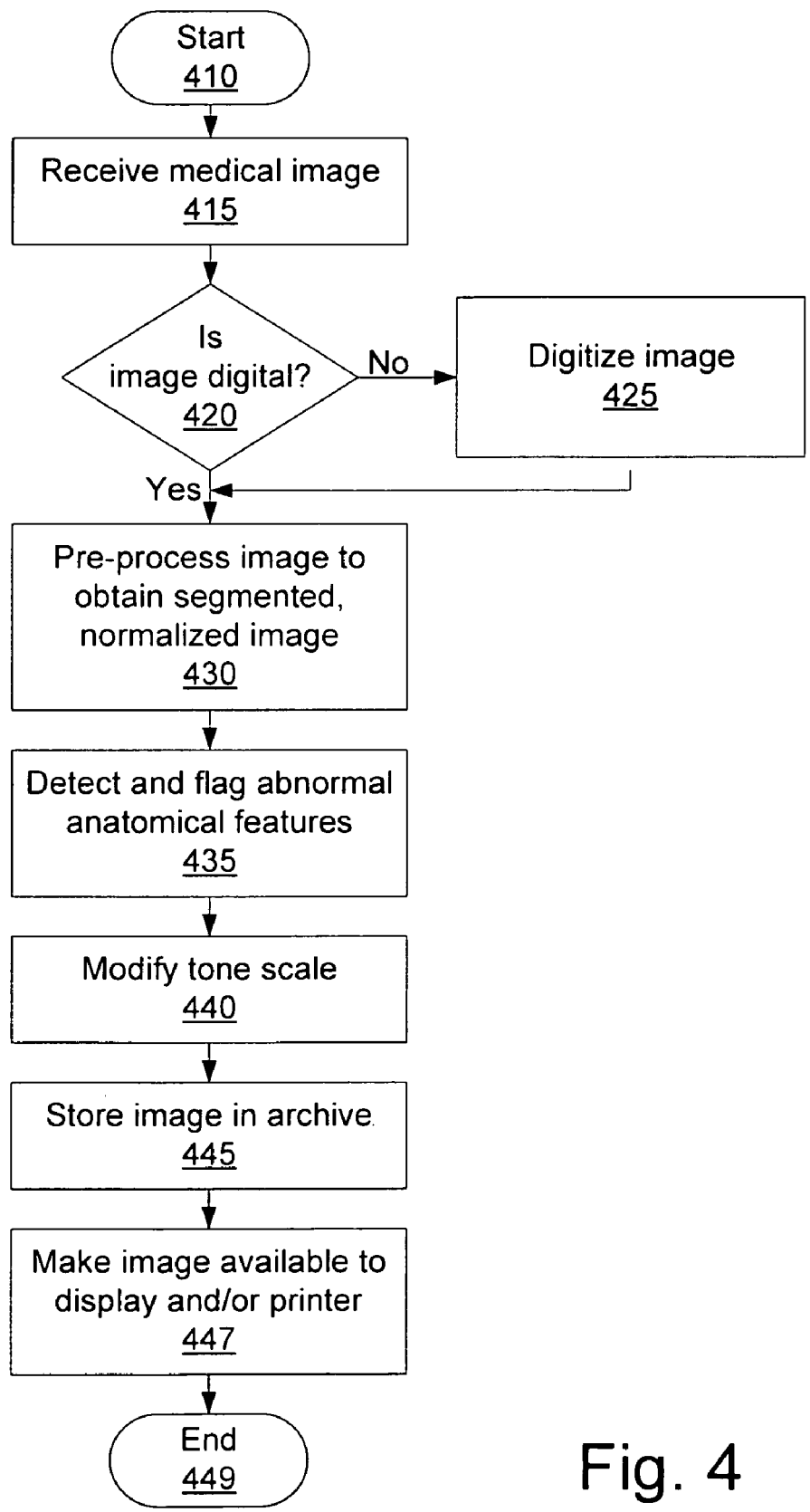
FIG. 4 is a flowchart of one embodiment of the image processing.

FIG. 4 is a flowchart of one embodiment of the image processing. The process starts at block 410, when the imaging system receives data. At block 415, the medical image is received. In addition to the data, additional information such as patient data, and historical data about the patient may be received as well. Additionally, data regarding other images that may be used for analysis may be received or retrieved by the system as well. For one embodiment, each patient has a unique identifier, such that the system may, in response to receiving a medical image, retrieve the related data from a database.

At block 420, the process determines whether the image comes from a digital or analog capture device. The image may be taken by a digital mechanism. Alternatively, the image may be taken on film or other analog media. For example, for mammograms and X-rays, the image is generally on a sheet of film. If the image is not digital, the process, at block 425 digitizes the image. For one embodiment, the Lumisys 85 system, by Kodak Corporation may be used to digitize the image. Note that images that have not been processed, whether analog or digital, are referred to as "raw images" compared to "processed images." Thus, an analog image is referred to as a raw image after it has been digitized, before any image processing operations are applied.

At block 430, the image is pre-processed to obtain a segmented, normalized and contrast corrected image. The process of normalizing and contrast correcting image is described in more detail below with respect to FIG. 6. Contrast correcting an image means transforming the incoming gray levels, whatever the image source, to the same contrast response and dynamic range. This "same" contrast response will be called the "canonical" contrast response. Normalizing the image means transforming the incoming gray levels, whatever the image source, usually by adding or subtracting a simple constant, so all images will have a range of gray values approximately having the same or similar mean value, or same or similar mean value over a limited area of the image. This is important in the preparation of the image for CAD processing because computer-aided detection algorithms are designed to detect changes in contrast or "signal", caused by changes in x-ray attenuation through an object and consistent performance regardless of image source is a very desirable feature. These changes indicate an abnormality such as a lesion in a mammogram or lung, and assume a single source, and thus consistent response to an identical signal. By normalization and contrast correction, images from all types of image acquisition devices are set to a canonical response curve, permitting the use of the same analysis programs regardless of the image acquisition method.

Hence, in order to properly assess a signal in the medical image, proper understanding of the response of the system to changes in input must be built into the algorithm. In this way, the algorithm can function properly even when receiving input from different sources. The different sources can be different types of film, various analog and digital sources. In addition, within one modality there is usually a certain amount of variability in technique that will affect the image quality.

For example, in mammography, the image can be acquired with variable x-ray energy (Kvp), and variable exposure (mas). The Kvp will affect the contrast and the exposure will change the overall level of the image. It would be beneficial to enable the accuracy of detection to be somewhat immune to these variables. As well as allowing operation in this more robust manner, the algorithm can, if desired, exploit the unique advantages of a particular detection system. A preferred method of performing this normalization and contrast response for two inputs—analog film and digital, will be described. The physics of imaging used in this section can be found in a standard reference such as Christensen et al. (An Introduction to the Physics of Diagnostic Radiology, Edward Christensen, Thomas Curry, James Dowdey, Lea & Febiger, Philadelphia).

In general, segmentation is the separation of the various elements in an image. Segmentation is an operation that assigns all image pixels that share some trait in common to a single class. As an example, segmentation algorithms such as described in U.S. Pat. No. 5,452,367 by Bick et al., may be used.

The appropriate process for the type of image is used, to produce the resultant output image. The image may be identified by a DICOM header, identifying the type of image being processed. For another embodiment, some other identification may provide the data. For another embodiment, an operator may manually key the data identifying the image type, i.e. mammogram, CT scan, chest X-ray, etc. For another embodiment, the system automatically detects the image type.

At block 435, the abnormal anatomical features are detected and flagged. Each medical image requires a separate process for such detection. Examples of this process for a mammogram are described in U.S. Pat. No. 4,907,156. An example of this process for chest radiography is described in U.S. Pat. No. 5,289,374. An example of this process for CT scan is described in U.S. Pat. No. 5,881,124. Alternative methods of detecting and flagging abnormal anatomical features may be used.

At block 440, the tone scale is generated. For one embodiment, the tone scale can only be generated for images that were originally received as raw images. If "raw" digital data is available, i.e., data that has not had a tone scale applied, or otherwise compressed in dynamic range, the CAD code can operate on the raw data and possibly perform better in very dense regions than if it operates on processed data. Similarly, the output display can be optimized by using the information from the raw data, as will be explained below, with respect to FIG. 7.

At block 445, the image is stored in an image archive. For one embodiment, the entire image is stored. For one embodiment, the image may be stored in a unified medical description of the patient, such as HALO (heterogeneous archival life object). For another embodiment, only some portion of the data may be stored. For one embodiment, only the processed image is stored, the flags indicating the abnormal anatomical features are not stored. For another embodiment, a complete report is stored.

At block 447, the image is made available for display and/or print. At this point, the reviewer—a radiologist or other medical personnel—can review the image, along with the flags and the enhancements discussed above. The image is used by the reviewer to make a medical determination.

Figure 5:
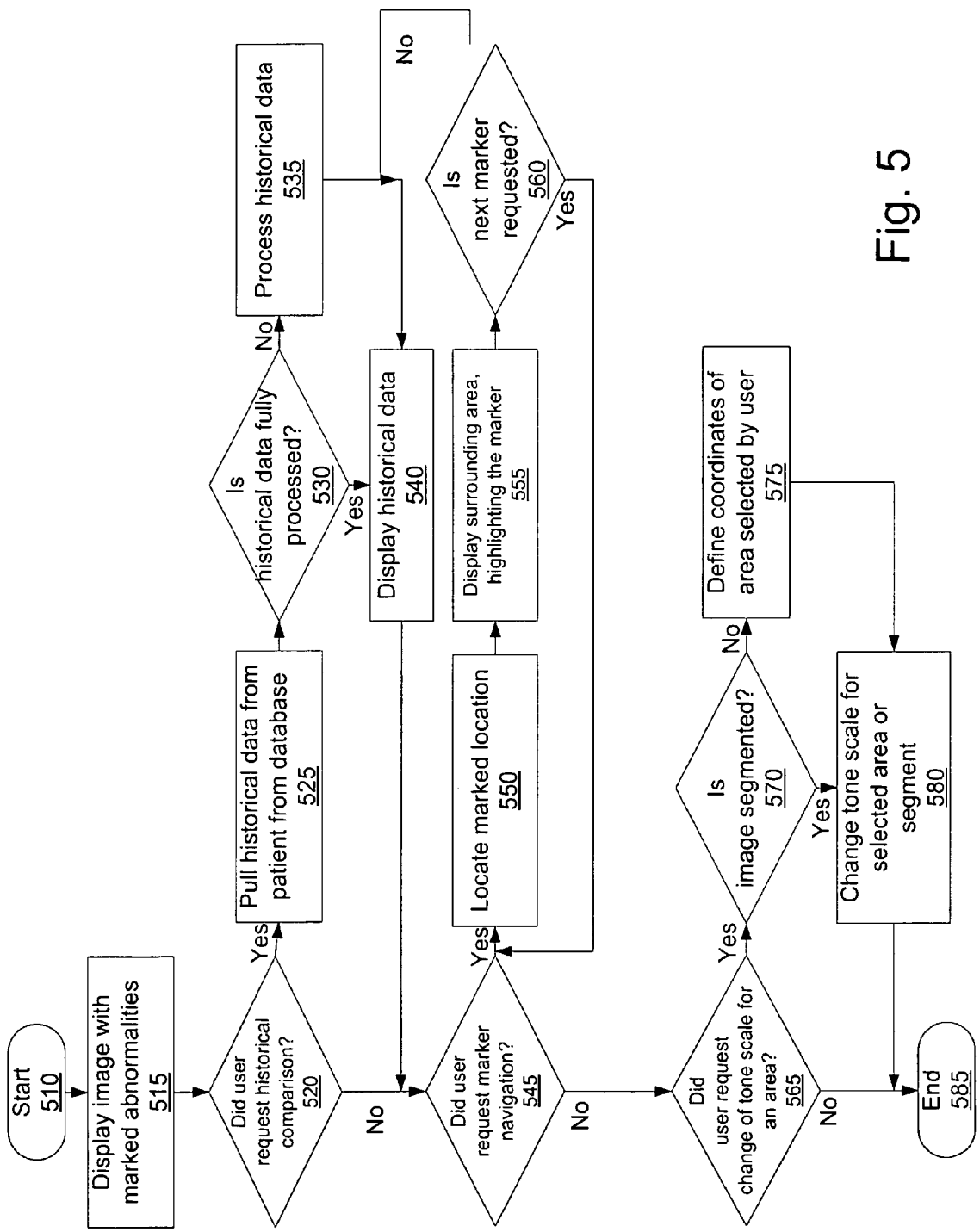
FIG. 5 is a flowchart of one embodiment of the display of the images.

FIG. 5 is a flowchart of one embodiment of the display of the images. The process starts at block 510, when a reviewer calls up a patient's record, including the medical images analyzed, as described above. This example describes the interaction with a digital display system. Of course, the image may be printed to film, and the traditional light table analysis may be used. Alternatively, the method described in U.S. Pat. No. 5,828,774 may be used, in which a digital display supplements a film printout.

At block 515, the image is displayed. For one embodiment, the image is displayed with the markers indicating the abnormalities found by the analysis logic. For another embodiment, the image may be displayed without the markers, or two images may be displayed, one with the markers, and one without the markers. For yet another embodiment, the markers may be displayed as an overlay, such that the markers are overlaid over the digital image. This may be controlled by the reviewer, by preset preferences, by a set up configuration file, or through other means.

The various options described below may be available to the reviewer. Although this is illustrated as various decision blocks, in fact the reviewer initiates any of these options. For another embodiment, one or more of these options may be set to run automatically. Thus, for example, a reviewer may set a preference to automatically do a historical comparison, or use marker navigation.

At block 520, the process determines whether the user requested a historical comparison. A historical comparison compares the existing image with historical data, or data from images obtained through different processes. In general, these images are stored in an archive, and are retrieved upon request.

If a historical comparison was requested, the process continues to block 525. Otherwise, the process continues to block 545. At block 525, the historical data is retrieved from the database. As described above, the patient may be uniquely identified to permit such access to patient data. For another embodiment, a single patient record may contain all such information, and this information may be already in memory when the primary image is being examined.

At block 530, the process determines whether the historical data is fully processed. The historical data may be a simple analog image, or may be a fully processed digital image. If the historical data is not fully processed, the process continues to block 535. At block 535, the historical data is processed. For one embodiment, this involves processing the data as described above with respect to FIG. 4. For another embodiment, the historical data may not be fully processed. For example, the historical data may be only normalized and segmented, but the abnormality detection process may not be run on the historical data. After processing, the historical data is displayed, at block 540. If the historical data is initially fully processed, as determined at block 530, the process continues directly to block 540.

The historical data may be displayed in a separate window. For example, the historical data may be displayed side-by-side with the primary image. For another embodiment, the historical data may be overlaid over the primary image, to further enhance the comparison. Alternative methods of displaying the historical data—for example by overlaying the markers from the historical data onto the primary data—may be used.

At block 545, the process determines whether marker navigation has been requested. Marker navigation permits the reviewer to move from marker to marker with a simple selection, or automatically. If marker navigation is requested, the process continues to block 550, otherwise, the process continues to block 565.

At block 550, the marked location is identified. The marked location may mark any anatomical abnormality flagged by the system. At block 555, the surrounding area, surrounding the marker is displayed. For one embodiment, a zoomed-in area is shown, such that the marker can be seen well. For one embodiment, the image may be automatically tone scaled, to display the area in question at an optimal tone scale. The process, at block 560, determines whether the reviewer has requested the next maker. In general, the reviewer may skip around the markers, or review the markers one after the other. If the next marker is not requested, the process stays at block 560. Of course, the user may request a historical comparison, a tone scale adjustment, or any other feature of the user interface this point. If the user requests the next marker, at block 560, the process returns to block 550, and identifies the next marker's location.

At block 565, the process determines whether a change of tone scale has been requested. The user may request a different tone scale for an image, to enhance the viewing of certain marked-up areas, or certain areas that are too dark or too light to be easily reviewed. If no change of tone scale has been requested, the process ends at block 585. Of course, as discussed above, these are not sequential requests, and thus the ending is merely indicated for simplicity.

If, at block 565, the change of tone-scale is requested, the process continues to block 570.

At block 570, the process applies a tone scaling. For one embodiment, if an image is segmented, the reviewer may request a change in tone scale for a particular segmented portion of the image. Otherwise, the user may select a portion of the image for which the new tone scale should be shown.

If the image is not segmented, the user may define an area for tone scale adjustment. The area may be selected using a mouse, using coordinates, or by defining a radius or area centered around a particular marker.

For another embodiment, the user may select a marker indicating a suspicious region, and a window displaying the selected marker and surrounding area, with an optimized tone scale, may appear.

Alternatively, the tone scaling may be by default. For example, bright areas may be always tone scaled down. Alternatively, dark areas may be tone scaled to permit better viewing. Any set of defaults may be established.

At block 580, the tone scale is adjusted for the selected area or segment. In this way, the reviewer's experience is enhanced, and the optimal review is permitted. This should increase the number of successfully identified abnormalities, and should make the radiologist or other medical personnel's job easier.

Figure 6:
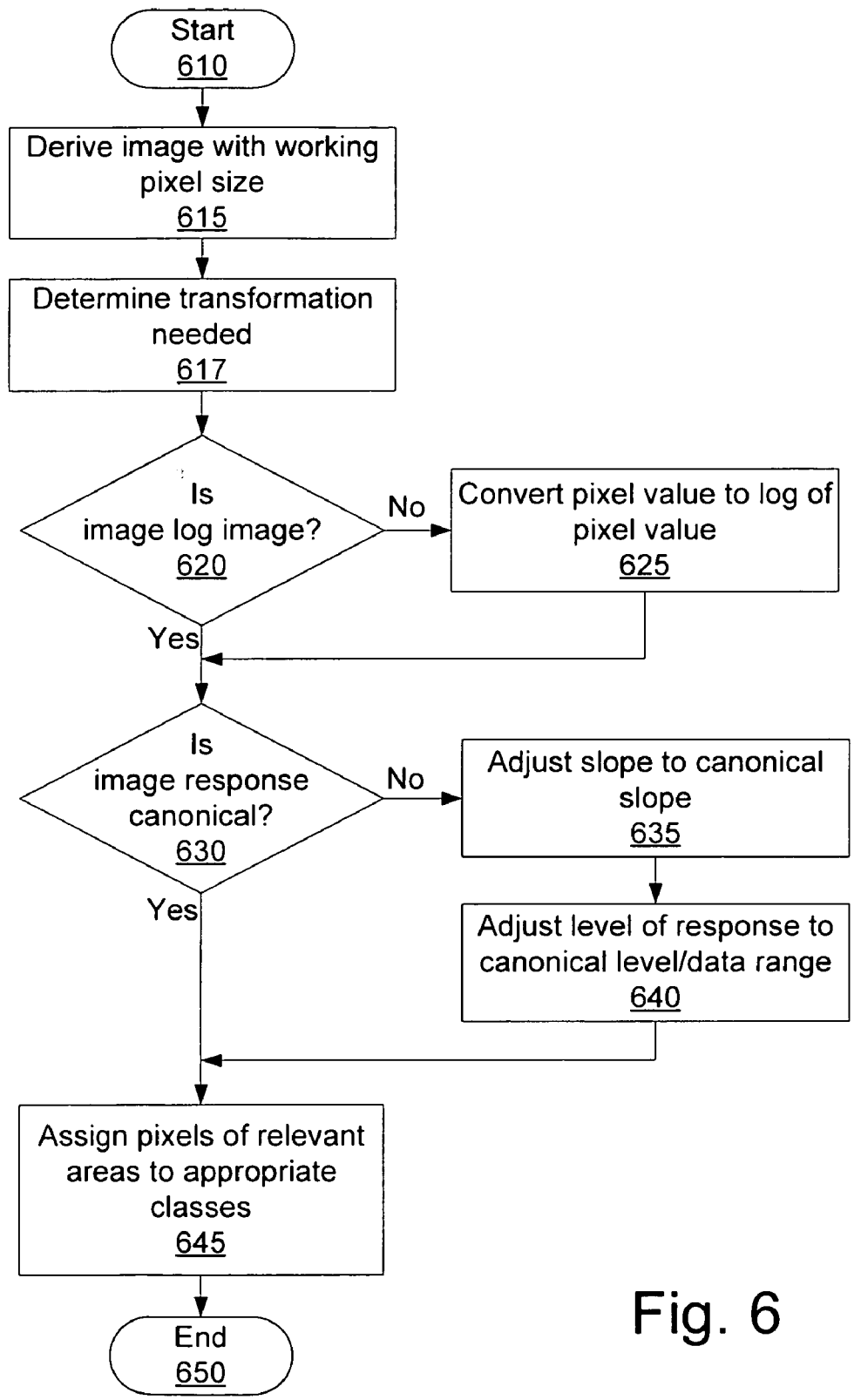
FIG. 6 is a flowchart of one embodiment of the preprocessing of the images.
Figure 7:
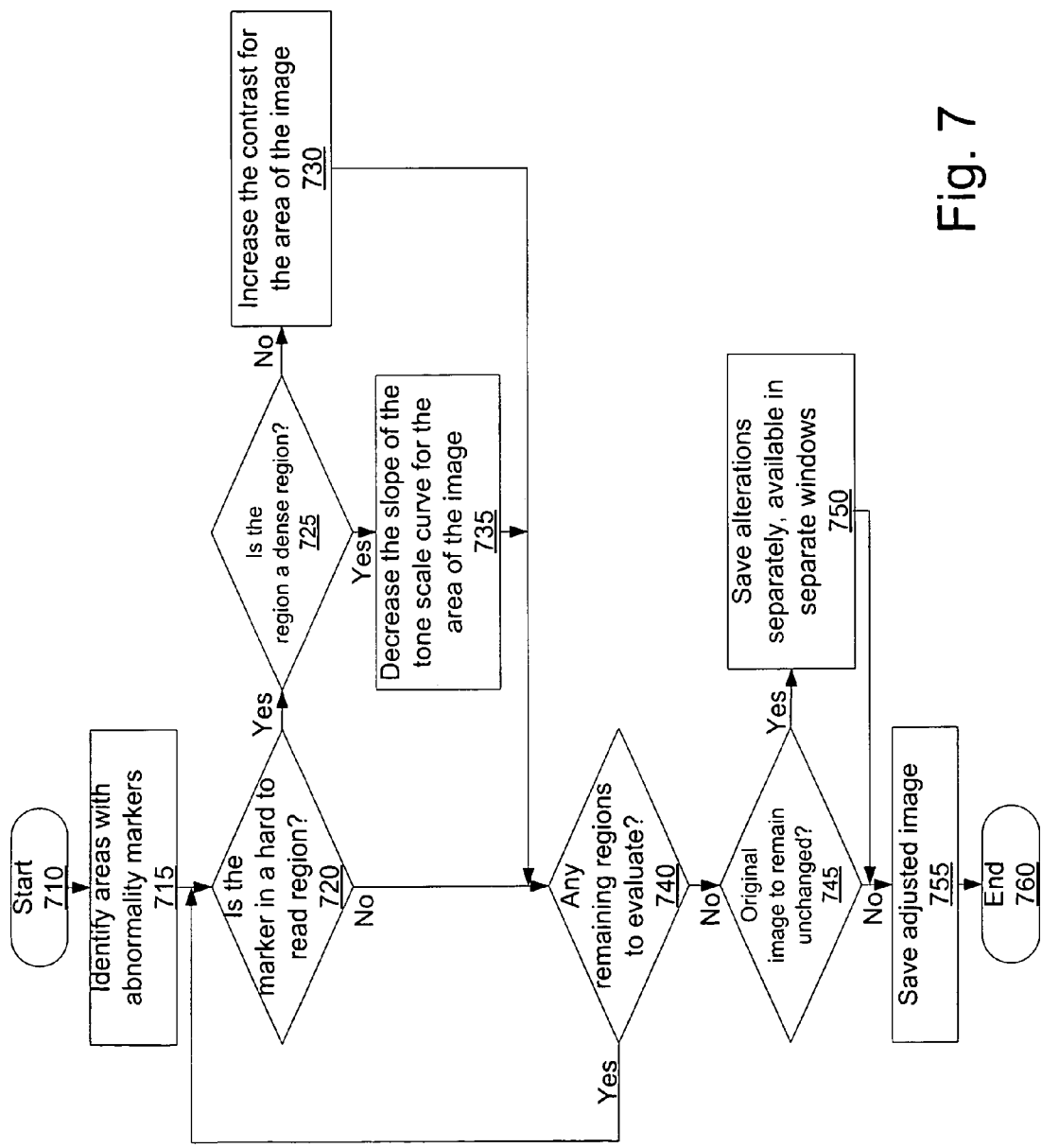
FIG. 7 is a flowchart of one embodiment of the post-processing of the images.

The processes described above with respect to FIGS. 1–5 apply generally to all medical images, regardless of modality and anatomical features being examined. It should be understood that these processes are modality and feature independent. However, an overview example discussing CT scans is described below with respect to FIG. 10, and a detailed example is provided below, in FIGS. 6 and 7 showing the pre- and post-processing used for a mammogram or a chest x-ray. These are merely exemplary processes. One of skill in the art would understand how to extend them to other modalities and features.

FIG. 10 is a data flow illustrating the various steps taken for a computer tomography (CT) scan. The image is received from a source. The source 1010 may be a digital CT scanner 1015 or a digitizer 1017, which takes film images taken by a standard CT scanner. The images are then scheduled automatically for evaluation.

The scheduler 1020 schedules an evaluation of the image. For one embodiment, the scheduler 1020 retrieves historical images for temporal comparison. For one embodiment, the scheduler 1020 interfaces with the image analysis system, to schedule the analysis of the data.

The scheduler 1020 passes the image to image analysis system 120, for temporal comparison 1030 and nodule detection 1040. Temporal comparison 1030 compares previous images taken of the same portion of the user's anatomy, to see changes over time. Nodule detection 1040 detects nodules in the image.

The automatic reporting logic 1050 receives the nodule data from nodule detection 1040 with the associated temporal data. This data is then used to automatically generate a report. The report, for one embodiment, identifies each of the nodules in the image, and classifies each nodule. For one embodiment, marker navigation permits a user to select a nodule in the report, as automatically generated, and navigate in the CT scan image(s) through selecting a nodule in the report. In this way, the report and the images are tied together. Note that although not specifically discussed, the CT images may be preprocessed and post-processed, as discussed above.

FIG. 6 is a flowchart of one embodiment of the preprocessing of the images. The process starts at block 610. The process starts when a new image is received for processing. This may occur immediately upon taking the medical image, or may occur later.

At block 615, an image with a working pixel size is derived. This process turns the pixel resolution of the incoming image into the resolution needed for the computer aided detection algorithm. Typical pixel sizes for digital mammographic detectors are 86 micron (amorphous Selenium detectors), 50 micron (computed radiography or CR detectors), and 100 microns (Cesium Iodide), while the best commercial film digitizers typically digitize mammograms with 50 micron pixel sizes. Chest detectors available today have pixel sizes of 183 micron, 86 micron, and many other sizes, and chest films may be digitized at many resolutions from 50 microns and up.

The actual pixel size and number of pixels in an image can be stored in a header associated with the image, or, as in our preferred embodiment, they can be stored in the DICOM header that is sent with the image into the digital system. The operation of turning the incoming image resolution into the resolution used by the internal algorithm of the digital system is essentially that of "resampling" the incoming array into a different output array, through smoothing or interpolation filters, see for example a standard reference for such image processing operations (Anil K. Jain, Fundamentals of Digital Image Processing, Prentice Hall).

At block 617, the process determines the transformations needed to obtain a canonical contrast response. For one embodiment, this is determined based on the image source. Generally, the contrast response is a direct function of the image acquisition mechanism. Thus, based on the known image acquisition mechanism, the processes needed for adjusting the contrast response may be identified.

At block 620, the process determines whether the image is a linear image or a log-linear image. If the image is a linear image, the process continues to block 625. At block 625, the pixel values for the image are converted to the log of the pixel values.

At block 630, the process determines whether the level of response is at a canonical level. For one embodiment, this determination is done by identifying the source of the image, and determining whether the source requires normalization. For one embodiment, normalization levels for each type of available input are precalculated, based on empirical testing. The calibration method used to set these measurements is described below. The "canonical" contrast response and dynamic range is determined based on a particular value for the particular anatomical feature being imaged. This value may be set based on the first images collected during CAD development, or at another stage of development.

If the level of response is already at the canonical level, the process continues directly to block 645. Otherwise, the process continues to block 635.

At block 635, the slope of the image response is adjusted to a canonical slope. At block 640, the level of response is adjusted to the canonical level and data range. An example of these conversions is discussed in more detail with respect to three examples. The response of x-ray film is linear with log relative exposure:

$$OD = \gamma \log(E/E') \quad \text{(Equation 1)}$$

The term "canonical" response is actually just Equation 1, i.e. a log-linear response to exposure, with a particular value of "slope" and a particular intercept determined by the parameter E'. The examples below describe how to transform various alternative inputs into the canonical form given by Equation 1. They cover the expected spectrum of data sources, which include:

a) Transforming a response that is linear with respect to exposure, typical of many digital sources.

b) Transforming one linear response to another linear response, i.e. one digital detector into another digital detector c) Transforming a log response, like equation 1 but with different parameters $\gamma$ and E', into the canonical log response. This may be used, for example, if two types of film/screen are being put into similar form, or in the case of digital detectors that do not output linear (raw) data, but data processed at least to the point of having a log applied.

Where the slope of the response is typically close to 3 for mammographic film, and dose to 2 for chest film. OD, or optical density, is the standard measure for darkness of the film. The range of OD varies with the type of film, but can vary from 0 to 4.2 for modern mammographic film. The maximum value of OD a film can attain is called "Dmax". An equation that relates film OD to pixel value of the digitized image is given by:

$$PV = PV_{max} - OD(PV_{max}/Dmax) \quad \text{(Equation 2)}$$

Pixel value PV, reaches a maximum value of $PV_{max}$ when the film is clear, or OD=0. When OD reaches its darkest value, Dmax, PV will be 0. Combining equations 1 and 2, digitized pixel value is related to log relative exposure by the following:

$$PV = PV_{max} - (PV_{max}/Dmax) * \gamma * \log(E/E') \quad \text{(Equation 3)}$$

This response is approximated in FIG. 9A. This curve, called the H&D, or "characteristic" curve, or occasionally "tone scale" in radiology, shows that the response to log relative exposure does not remain linear indefinitely, as suggested by the equation, but flattens out at both ends. The regions of non-linearity at the ends are called the "toe" and "heel". Hence, film has a linear response to the exposure only over a limited range. The important features of this curve are it's slope or "gamma", and it's "latitude" or dynamic range, both of which are characteristics of the film. The greater the gamma, the higher "contrast" is the film—i.e., for a given change in exposure, the larger will be the change in signal or pixel value. However, the maximum range that the OD, and ultimately the pixel value can take is limited by the dynamic range of the visual system. Currently a Dmax of 4.2 is close to the limit of darkness that can be visualized given the brightness of light boxes. This means that there is a contrast-latitude tradeoff. That is, increase in contrast or slope of the curve will result in a corresponding loss of latitude such that the Dmax will remain close to the limit.

Similar limitations will exist for display of an image on a CRT monitor. Due to the monitor's limited dynamic range, an increase in contrast will result in a decrease in latitude. The significant point is that any display device will have limited dynamic range and limited contrast, and it is the aim of this invention to ameliorate this limitation to some extent. Secondly, the signal strength of a given image feature is a function of the exposure level of the x-ray as shown in the equation following:

$$I = I_o * \exp(-\mu z) \quad \text{(Equation 4)}$$

This shows that the flux (I) of x-rays passing through an object is proportional to the flux incoming ($I_o$), and decreases exponentially with $\mu$, the attenuation of the object, and z, the thickness of the object. The attenuation is a function that decreases with increasing energy, and hence the same object will have less contrast when exposed to higher energy x-rays. The following discussion will show how the pre-processing functions can correct the contrast and create a particular response that is desired. Note that the above discussion is slightly simplified, assuming monoenergetic x-rays. However, the basic principles discussed above do not change for other types of x-rays. The above calculations can be modified, as would be understood by one skilled in the art, to explain standard x-ray behavior.

Next, the response of a direct digital detector will be described, and how the system will "normalize" its response to be similar to the film response above. The raw pixel value from a digital acquisition device responds linearly to exposure:

EXAMPLE 1

$$\text{Input} = PV_{raw} = gE \quad \text{(Equation 5)}$$

In order to map this response to the form of equation 3, three steps are taken:
a) raw pixel values are converted to Log pixel value
b) the contrast or slope is adjusted to the "canonical" slope
c) the response is normalized (the level is adjusted) to the "canonical" level or data range.

The first step in this procedure can be accomplished by using the equation:

$$PV = \log(PV_{max}/\text{input}) * PV_{max}'/\log(PV_{max}) \quad \text{(Equation 6)}$$

In equation 6, $PV_{max}$ is the maximum pixel value of the input data, often 14 bits for present devices, and $PV_{max}'$ is the maximum pixel value it is desired to map the input to, such as 12 bits. The dependence of PV on log of input is depicted as "curve 1" in FIG. 8B.

This response is going to be converted into the "canonical" slope desired. This can be accomplished by multiplying by a constant G chosen empirically to match slopes with the desired "canonical" response of equation 3:

$$PV = \log(PV_{max}/\text{input}) * PV_{max}'/\log(PV_{max}) * G \quad \text{(Equation 7)}$$

Figure 9B:
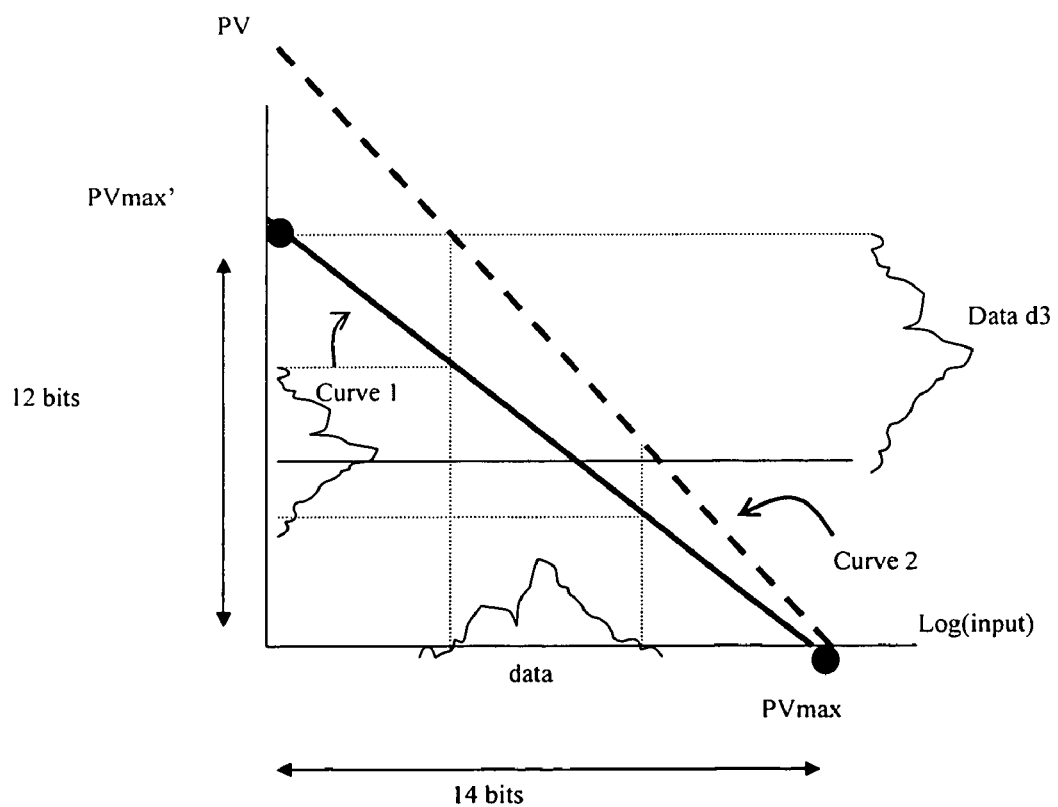

This is depicted as "curve 2" in FIG. 9B, which shows how the original data is mapped into "data d3" which has the correct "contrast" or slope response.

What has been effectively done is to present a method of taking an arbitrary response curve, characteristic of the detector, and "standardize" the contrast, making it uniform across all films or detectors on which these measurements are performed.

Finally, it is desired to move the range of the data to the desired range. This insures that the image has the correct "mean" pixel value. This is sometimes accomplished in detector hardware with auto-exposure detectors, which shut off the exposure at a desired level. In the present system, this is accomplished by adding a shift factor X to the PV in equation 7, which yields the final form of the desired transformation:

$$PV = [\log(PV_{max}) - \log(\text{input})] * PV_{max}'/\log(PV_{max}) * G - X \quad \text{(Equation 8)}$$

This shift is equivalent to setting the overall "OD" of the image to the user's preferred standard. With equation 8 the full form of the transformation from digital to film type response is obtained. The above discussion explains in principle how to obtain the two free parameters: the gain factor G, and the shift factor X.

One difference between digital and film response is important for the discussion below. Digital detectors have much larger latitude than film. The practical consequence of this is that in dense anatomic regions where the film response begins to "clip", as seen in FIG. 9F, the digital response will continue to be linear. This is taken advantage of, as described with respect to the post-processing section below. If "raw" digital data is available, i.e., data that has not had a tone scale applied, or otherwise compressed in dynamic range, the CAD code can operate on the raw data and possibly perform better in very dense regions than if it operates on processed data. Similarly, the output display can be optimized by using the information from the raw data, as will be explained below in the post-processing module.

In order to further clarify the above equations, an example is provided, showing how the slope of the response curves 6 and 3 can be set to the same value. Equation 3 says that the slope of the curve is given by:

$$S = -(4095/Dmax) * \gamma \quad \text{(Equation 9)}$$

The slope can be calculated without knowing the exact values of Dmax and $\gamma$, but it can be assumed for the purposes of this example that Dmax=4.2, and $\gamma$=3. Then the slope is $-2925$. Converting the log base 10 to natural log:

$$PV = 4095 - 1272 * \ln(E/E') \quad \text{(Equation 10)}$$

The assumption can be made, without loss of generality, that the maximum pixel value is 12 bits, e.g. 4095. An example will illustrate the significance of the slope value 1272. Assume that a step wedge such as shown in FIG. 9G is exposed, the film is developed and digitized, and the pixel value PV behind each step is measured. The result would be:

$$E1 = E_{in} * \exp(-\mu z)$$

$$E2 = E_{in} * \exp(-2 \mu z), \text{ and so on. Therefore,}$$

$$PV1 = 4095 - 1272[\ln(E_{in}/E') - \mu z]$$

$$PV2 = 4095 - 1272[\ln(E_{in}/E') - 2 \mu z] \text{ etc}$$

Therefore the difference in pixel value between two adjacent steps is:

$$\Delta PV = -1272 \, \mu z \quad \text{(Equation 11)}$$

Figure 9C:
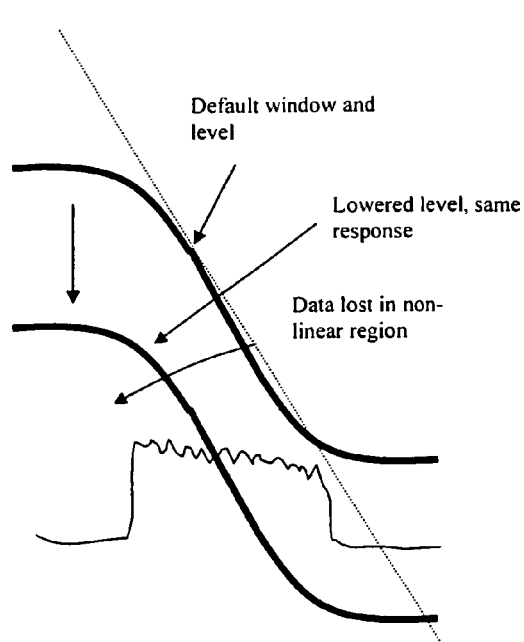
Figure 9D:
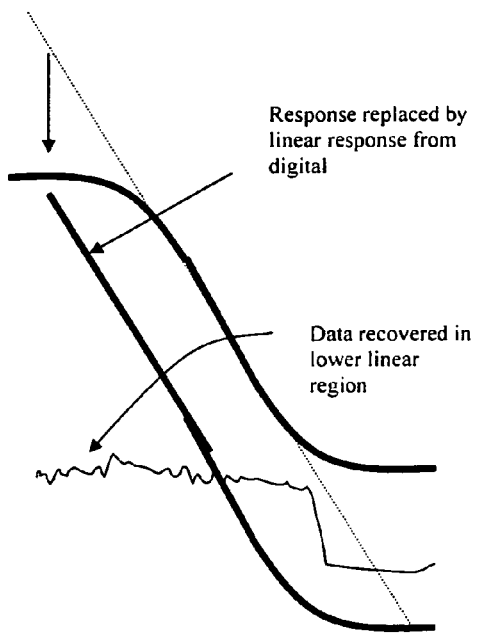
Figure 9E:
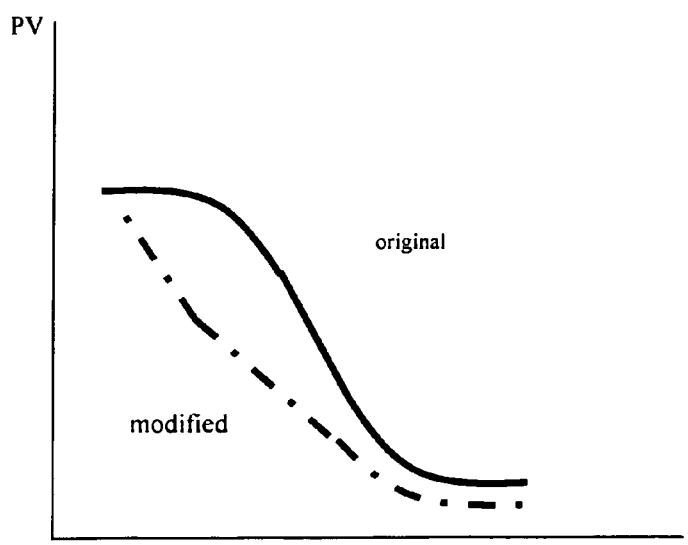
Figure 9F:
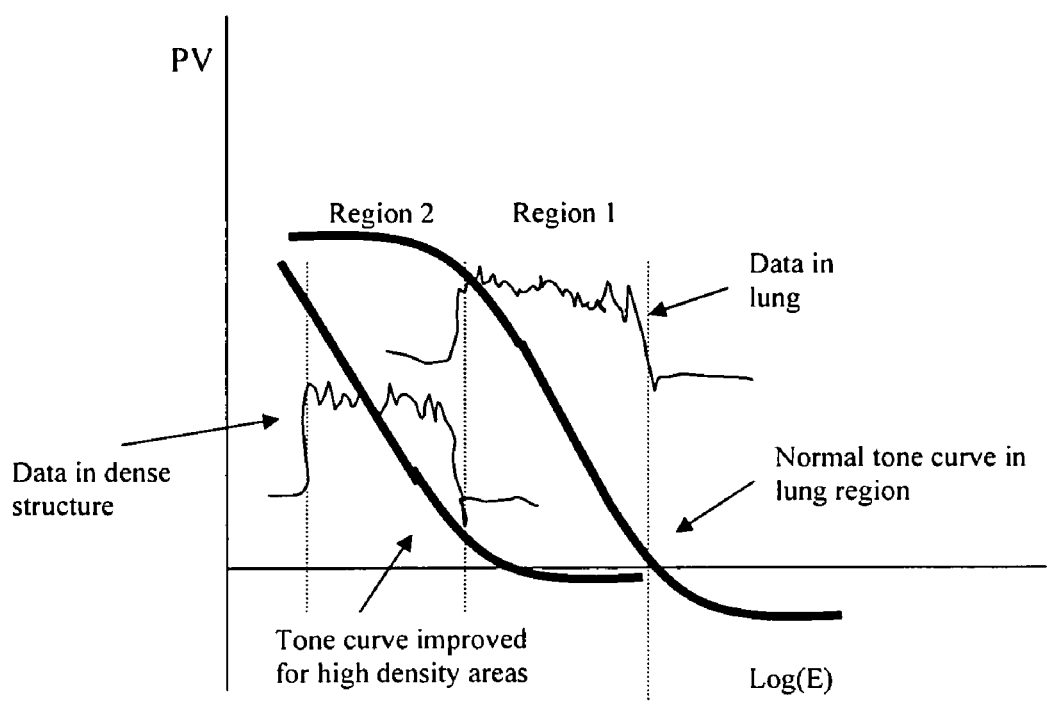
Figure 9G:
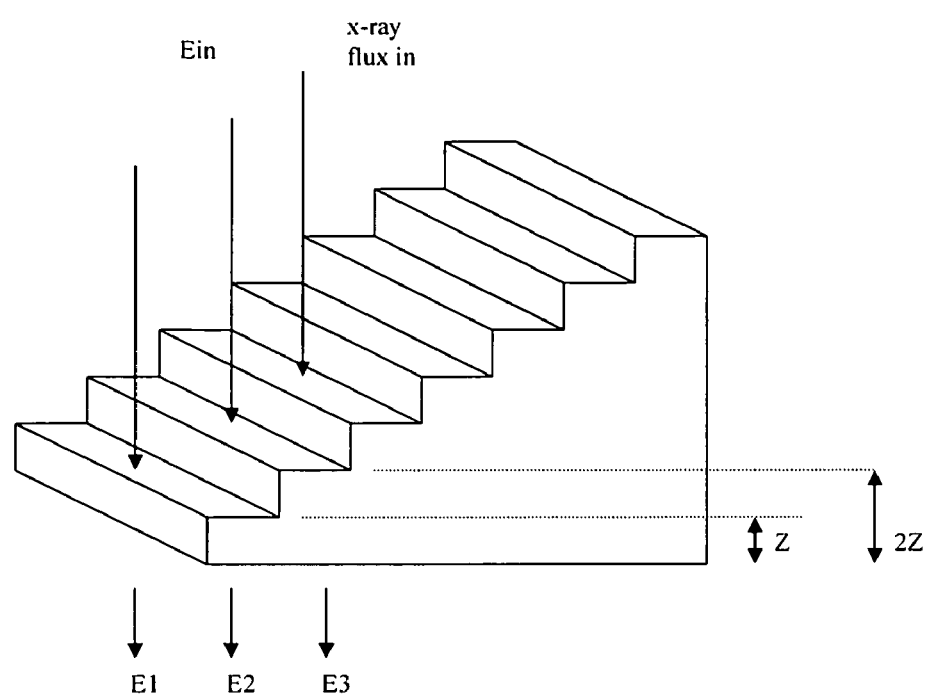
Figure 9H:
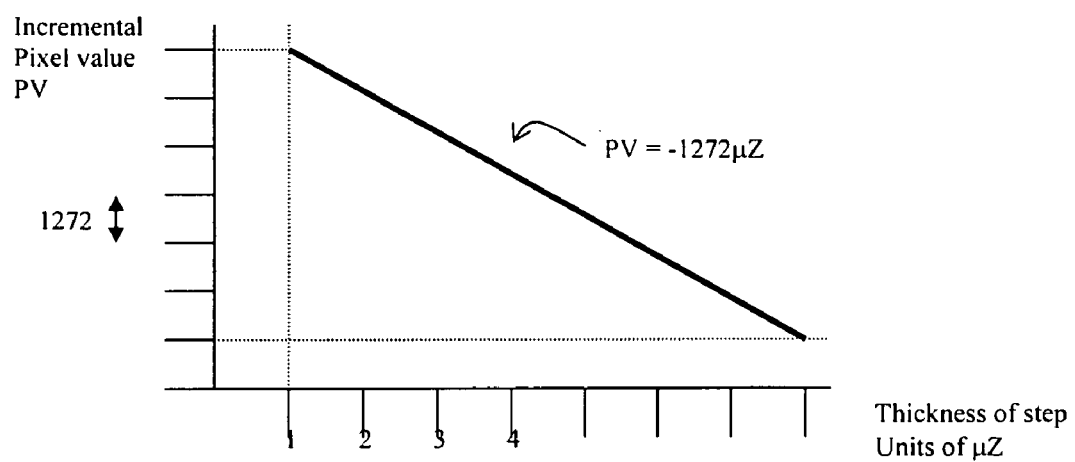

This "canonical" slope is shown in the curve in FIG. 9H. It can be appreciated that the slope can be a value other than 1272 so the assumptions above are not limiting. Now the same measurement can be repeated with the same step wedge on a digital detector with response given by equation 6.

$$PV = [\ln(PV_{max}) - \ln(\text{input})](PV_{max}'/\ln(PV_{max})) * G$$

Without loss of generality, assume $$PV_{max} = PV_{max}', \text{ so}$$

$$PV = PV_{max} G - \ln(\text{input}) * G * PV_{max}/\ln(PV_{max})$$

Or, for 12 bits max, $$PV = 4095 G - \ln(\text{input}) * 492 G$$

Using the same step wedge, $$\text{Input1} = gE_{in} * \exp(-\mu z)$$

$$\text{Input2} = gE_{in} * \exp(-2 \mu z),$$

So $$PV1 = 4095 G - 492 G[\ln(gE_{in}) - \mu z]$$

$$PV2 = 4095 G - 492 G[\ln(gE_{in}) - 2 \mu z], \text{ etc, so}$$

$$\Delta PV = 492 G \, \mu z$$

By comparing with equation 7, the value of G may be set such that the slope of the response from digital equals that of film/screen. In this example, G=2.58, but in general the slopes may be set to any "canonical" value.

EXAMPLE 2

Next, consider the pre-processing changes required to accommodate a different digital detector, with a different gain. Suppose two detectors with different responses are used. The responses are given by:

$$Input_1 = g_1 * E$$

$$Input_2 = g_2 * E$$

Using equation 8 then gives:

$$PV_1 = 4095G - ln(input_1)*G - X = 4095G - ln(g_1 E)*G - X$$

$$PV_2 = 4095G - ln(input_2)*G - X = 4095G - ln(g_2 E)*G - X$$

So $$\Delta PV = PV_2 - PV_1 = ln(g_2/g_1)*G \quad \text{(Equation 12)}$$

That is, changing to a detector with a different gain can be taken into account with a simple shift in pixel value which will automatically be performed when equation 8 is performed with the correct shift (X) to normalize the 2 sets of data. It remains to describe the best way to obtain the shift value X.

As discussed above, the shift is equivalent to setting the overall "OD" of the image to the user's preferred standard. For the preferred "canonical" level, a pixel value of 2400 is chosen, which is equivalent to a film OD of approximately 1.6. Therefore, in one embodiment, a "contrast" or "slope" of −1272 is selected in conformance with equation 9, and a "mean" pixel value of 2400 is selected, which determines the shift value X in equation 8. The "mean" pixel value used in the system is the mean inside of the anatomy being studied and therefore uses segmentation of the anatomy. For mammograms, the mean value is the mean inside of the breast, for chest x-rays it is the mean value within the lung field.

EXAMPLE 3

One final example will suffice to cover all the cases anticipated, and that is the proper normalization for a different film response, or a digital "processed" data. In many of the commercial devices (such as chest CR machines) on the market today, the raw digital data is not archived, and in some cases cannot be communicated to a system such as this invention. In that case the images typically already have a tone scale applied, which makes the data response similar to equation 1, but in general with a different value of slope or y. Therefore, the problem is reduced to determining how to make a "film-like" response equivalent to the "ideal" response with the "canonical" slope (1272 above), and mean PV. From equation 1:

$$PV = 4095 - (4095/Dmax)*\gamma * \log(E/E')$$

A value of Dmax of 4.2 and γ of 3 are assumed. However, if this changes, a different slope is obtained. From equation 1, $$PV_1 = 4095 - 1272 * ln(E/E')$$

Would change to:

$$PV_2 = 4095 - S * ln(E/E')$$

The new value of slope can be determined in the same way it was above for film, using the step wedge of FIG. 9G. In this case, the difference in pixel values between steps that would be obtained is:

$$PV_2 = -S \mu z$$

The response of the equation 13 can then be simply turned into the standard response of 12 by multiplying with a gain factor:

$$G = 1272/S$$

As the above examples demonstrate, by adjusting the values to canonical values, the images obtained on different films or different digital images result in a canonical display. Thus, the image analysis system would not be confronted with images having different response levels.

At block 640, image correction is performed. Image correction may correct for tilt, noise, or other image faults.

At block 645, pixels of relevant areas are assigned to appropriate classes. The "mean" pixel value used in the system is the mean inside of the anatomy being studied, therefore segmentation of the anatomy is performed. The process then ends at block 650.

FIG. 7 is a flowchart of one embodiment of the post-processing of the images. The process starts at block 710. For one embodiment, if the image is a processed image, the post-processing operations described in this section are not applied and the system is not able to exploit the wider latitude of digital to help optimize the display. In this case, the post-processing module will be bypassed, and the display will be shown with whatever tone scale was applied by the acquisition device, and only have the usual windowing and leveling capabilities. However, if the image is raw, the post processing can improve the quality of the image displayed, and provide additional options to the reviewer.

The post-processing module applies a unique tone-scale to the image based on the finding of the computer-aided detection module or pre-processing module before it. As explained above, Equation 1, showing film OD as a function of log relative exposure, is one example of a "tone scale". The tone scale is broadly speaking a mapping of incoming x-ray exposure to a visual display according to some criterion such as optimal image quality or acceptability. This method obtains a new tone scale based on the requirement of visualizing a suspicious region or feature that is in a part of the data in the (hard to visualize) non-linear region of FIG. 8A, usually representing dense anatomy.

In mammograms, this hard-to-visualize region is typically found in dense parenchymal regions of the breast. In chest radiographs, the dense area would be in the mediastinem, heart, or diaphragm. Because these parts of the anatomy usually fall into the non-linear regions of the tone scale, a suspicious feature, such as a nodule or lesion, will be difficult to see on the display device or film, because the contrast of the image will be very low in the region.

On the other hand, it is necessary to limit the dynamic range of the image in some way, because all displays have limited dynamic range, whether they are films on light boxes or soft-copy monitors. The characteristic curve in FIG. 9A is typical of the tone scale mapping for diagnostic radiography. For diagnostic radiography, the compromise between visual contrast and dynamic range usually imposes serious constraints on the desirable tone scale. The optimal tone scale depends on the observer's interest, the characteristics of the display system, and what is new with this invention, the existence of an object that is important to see.

Figure 8C:
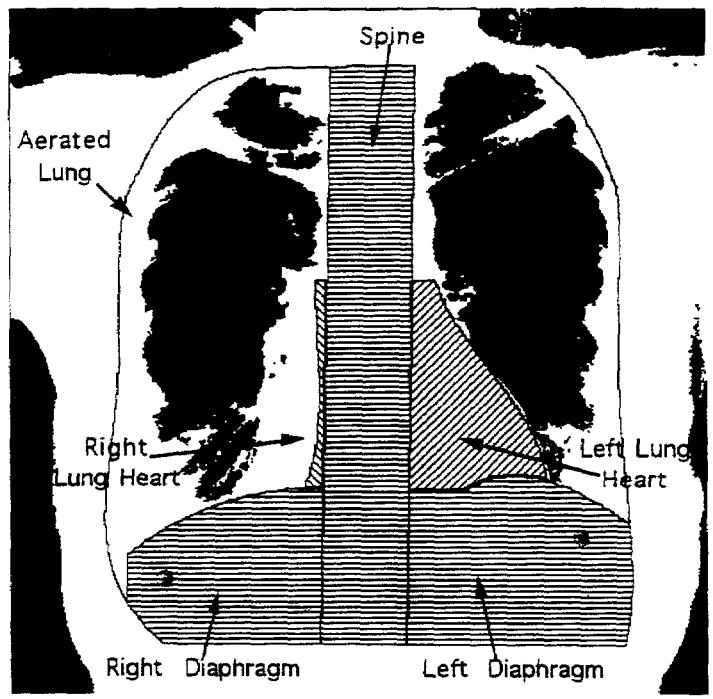
Figure 8D:
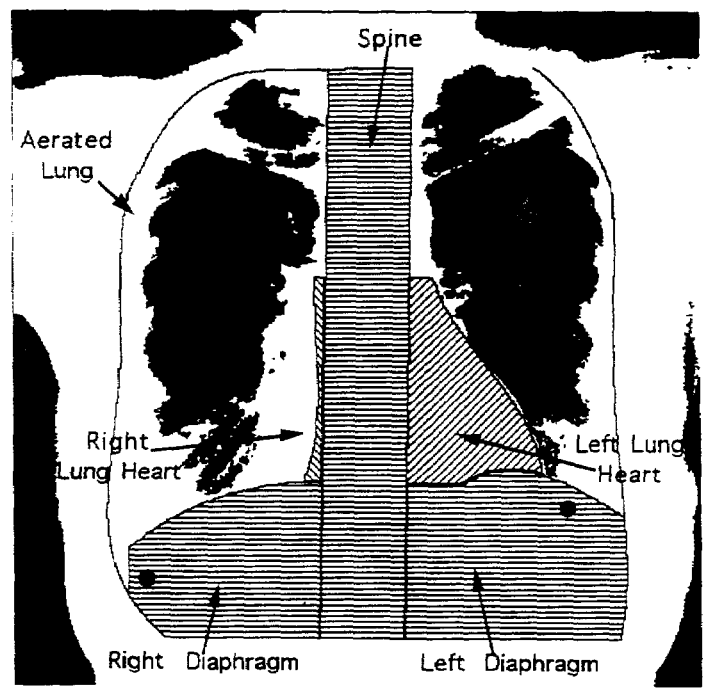

At block 720, the process determines whether the marker being focused on by the reviewer is in a hard-to-read region. Because the dynamic range must be limited before display, it sometimes happens that the image "saturates" at dense parts of the anatomy, and equal contrast objects (physically) appear very low contrast visually, or disappear all together. Such regions may include the mediastinem, diaphragm, and heart region in the chest radiographs shown in FIGS. 8C and 8D, or in the dense part of a mammogram shown in FIGS. 8A and 8B.

If the marker is in a hard to read region, the process continues to bock 725. At block 725, the process determines whether the region is a dense region.

Because the CAD algorithm does not require visualization to detect suspicious regions such as nodules, it can maintain good performance over a much larger dynamic range than would be permitted by visualization. If the CAD algorithm has found a region of interest, such as a nodule, in a region that would normally be difficult for the radiologist to visualize on a monitor or on film, the computer can employ a different tone scale such that that region can be visualized. This modified tone-scale might be implemented as an optional feature in the user interface—such as a button that will allow either the standard tone scale, or one of the modifications detailed below. The button may allow the modified tone scale to be displayed when appropriate, or it could toggle between modified and original tone scale. Various implementations of the modified tone scale might be implemented in the following ways:

If the region is a dense region, the process continues to block 735, and the slope of the tone scale curve is decreased. If the region is not a dense region, the contrast for the dense area is increased, at block 730. As shown in FIG. 9E, one can decrease the slope of the tone scale curve over the darker regions of the image, and increase the contrast in the brighter portion. The process then continues to block 740, to evaluate any remaining regions. If there are remaining regions, the process returns to block 720. Otherwise, the process continues to block 745.

One can produce a "window" associated with the CAD marker—a region of the image using larger contrast with the level decreased to an optimal level. That is, when the CAD code finds a suspicious region, it typically puts a marker on that location of the image, and puts the mark's coordinates in the CAD output object. In some display implementations using CAD, a button may be available in the user interface that allows more detailed viewing of a small region on the image—this button is often represented as a magnifying glass. By selecting (clicking) the button and then selecting the location of the CAD located abnormality, a window can pop up showing that region but with the improved tone-scale if it is in a dense region.

At block 745, the process determines whether the image remains unchanged, or whether one or more areas have had their tone scale or contrast changed. If the image has been changed, the process continues to block 750, where alterations to the original image are saved. For one embodiment, these adjusted image portions are saved in separate windows, such that if a user opens a focus window, the adjusted images are shown. At block 755, the adjusted image, whether including the alterations or not, are saved, and the process ends at block 760.

As shown in FIGS. 9C and 9D, one can leave the default image unchanged, but allow the level of the window and leveling function to bring in the signal in the dense region when the response level is lowered. In principle, this may be done without abnormality detection, but that would require the creation of a normalized version of the raw digital image.

Figure 8E:
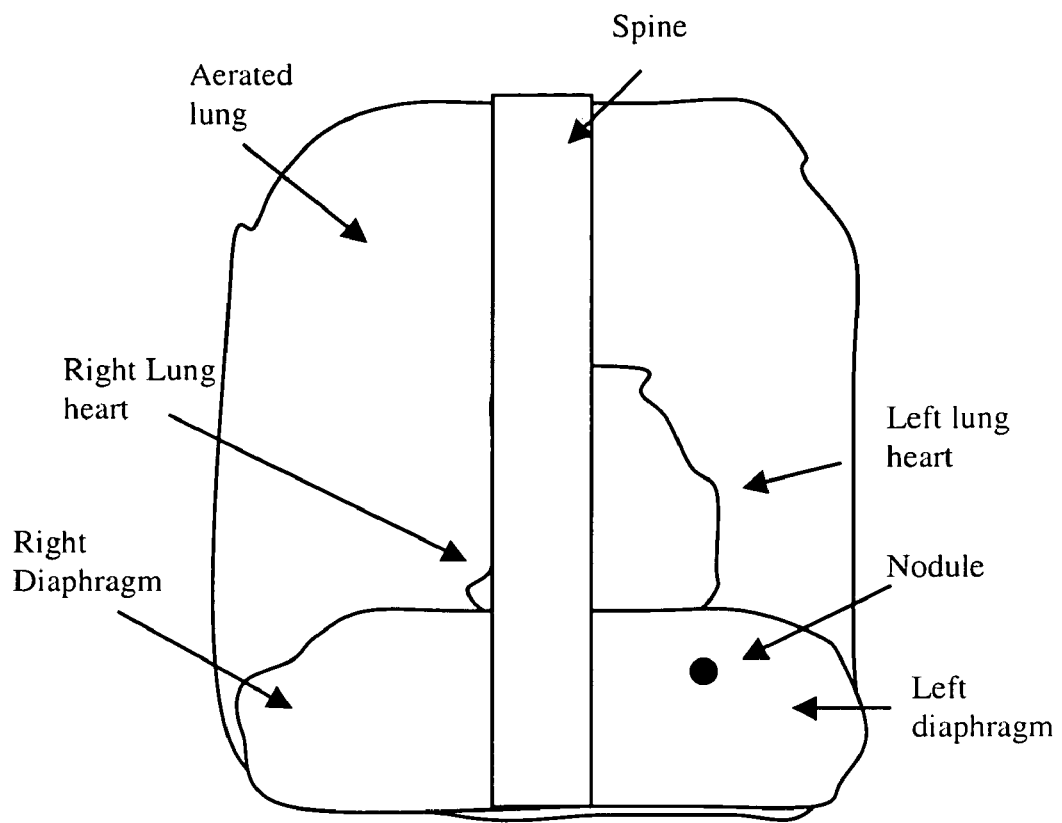

As shown in FIGS. 8E and 9F, one can use the result of a segmentation code to separate the lung field from the other anatomy, and apply a different tone scale to parts of the anatomy that differ greatly in mean exposure —e.g. the lung field from the heart and diaphragm. Care must then be taken to smoothly transition from the gray values of one region to the next.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method of analyzing a medical image to use a CAD system to detect anatomical abnormalities obtained from one of a plurality of original sources, the method comprising:
  providing a computer-aided detection (CAD) system configured to numerically process a medical image for identifying anatomical abnormalities therein, the CAD system having been trained using a training image set obtained from a first of said original sources;
  defining a canonical contrast response curve based on the training image set and the first original source;
  normalizing each medical image such that each medical image conforms to the canonical contrast response curve for image analysis regardless of the original source of the medical image; and
  numerically processing each of the normalized medical images using the CAD system to identify anatomical abnormalities therein.

2. The method of claim 1, wherein the normalizing for each medical image comprises:
  identifying which of the plurality of original sources was used to capture that medical image; and
  remapping pixel values of that medical image in accordance with a predefined remapping process associated with said canonical contrast response curve and said identified original source.

3. The method of claim 2, wherein the medical image is in a DICOM format, and wherein identifying the original source comprises reading a DICOM header associated with the medical image.

4. The method of claim 1, further comprising:
  detecting what anatomical feature is represented by the image; and
  processing the image to detect abnormalities in the anatomical feature, in accordance with a detection process for that anatomical feature.

5. The method of claim 4, wherein detecting what anatomical feature is represented uses a header present in a DICOM format of the image.

6. The method of claim 1, further comprising:
  generating a new tone scale for the medical image for optimal visualization of abnormalities in dense anatomic regions.

7. An apparatus to improve medical imaging comprising:
  a computer-aided detection (CAD) system configured to numerically process a medical image for identifying anatomical abnormalities therein, the CAD system having been trained using a training image set obtained from a first of said original sources;

an image analysis system to define a canonical contrast response curve based on the training image set and the first original source, the image analysis system further to normalize a medical image to conform to the canonical contrast response curve regardless of an original format of the image; and the CAD system further to process the normalized medical image to identify anatomical abnormalities therein, thereby permitting a single analysis algorithm to be used on all images regardless of original source.

8. The apparatus of claim 7, further comprising:
an image acquisition module to acquire a medical image from one of a plurality of sources.

9. The apparatus of claim 8, wherein the image acquisition module is coupled to the image analysis system through a network.

10. The apparatus of claim 7, further comprising:
a review station to allow medical personnel to review the medical image after analysis.

11. The apparatus of claim 10, wherein the review station is coupled to the image analysis system through a network.

12. The apparatus of claim 11, wherein the review station comprises:
a user interface permitting the reviewer to manipulate the contrast and windowing of the image.

13. The apparatus of claim 11, further comprising:
marker focus system to permit a reviewer to automatically move from marked location to marked location on the medical image, wherein each marked location corresponds to an abnormality detected by an abnormality detection system.

14. The apparatus of claim 7, further comprising:
a system archive to store the medical images, including historical images of past procedures.

15. The apparatus of claim 7, wherein the image analysis system further comprises a pre-processing module.

16. The apparatus of claim 15, wherein the pre-processing module comprises a pixel size adjustor to adjust a number of pixels per square inch to a standard value.

17. The apparatus of claim 15, wherein the pre-processing module comprises a segmentation logic to segment the medical image.

18. The apparatus of claim 7, wherein the image analysis system further comprises a post-processing module.

19. The apparatus of claim 18, wherein the post-processing module includes a tone scale generator to adjust a tone scale to optimize viewing of dense portions of the medical image.

20. A system comprising:
a computer-aided detection (CAD) system configured to numerically process a medical image for identifying anatomical abnormalities therein, the CAD system having been trained using a training image set obtained from a first source;
a source of image data, each image in the image data having one of a multiplicity of spatial resolutions and a multiplicity of contrast responses;
a preprocessing module to normalize the image by transforming the image data into a "canonical" form with uniform contrast response, overall level and pixel size, the canonical form based on the training image set and the first source;
such that the image analyzed by a computer aided diagnosis system has a uniform contrast response regardless of the original source of the image the CAD further to numerically process each of the normalized images to identify anatomical abnormalities therein.

21. The system of claim 20, further comprising:
a post-processing module to modifying a contrast response curve of the image to improve visibility of suspicious regions.

22. The system of claim 20, further comprising:
a CAD module to process said data to detect abnormal anatomical features meeting selected criteria.

23. The system of claim 22, further comprising:
a display to selectively display annotation maps at positions corresponding to suspicious regions around the abnormal anatomical features detected by the CAD module.

24. The system of claim 20, further comprising:
a remote display to permit access to the processed image via a network.

25. The system of claim 20, further comprising:
a network coupled to the system, the network permitting a distribution of processing to multiple computing devices.

26. A system comprising:
a source of image data;
a preprocessing module transforming the medical image into a "canonical" form with a universal contrast response, overall level, and pixel size, such that the contrast response of the medical image is the same as other medical images in said canonical form;
a computer-aided detection (CAD) module to process the image data to detect abnormal anatomical features meeting selected criteria and to flag the abnormal anatomical features as suspicious regions;
a post-processing module to modify a contrast response curve of the image to increase visibility of the suspicious regions.

27. The system of claim 26, further comprising:
a window generation logic to open a separate window on a display to display a suspicious region; and
the post-processing module optimizing the contrast response curve for the separate window.

28. A system comprising:
a source of medical images, each image having one of a multiplicity of spatial resolutions and one of a multiplicity of contrast responses;
a preprocessing module transforming the medical image into a "canonical" form with a uniform contrast response, overall level, and pixel size;
a CAD module to process the medical image to detect abnormal anatomical features meeting selected criteria and to generate annotation maps identifying image portions corresponding to said abnormal anatomical features;
a post-processing module to modify a contrast response curve of the image to increase visibility of suspicious regions associated with the abnormal anatomical features; and
a display to selectively display annotation maps at positions corresponding to suspicious regions.

29. The system of claim 28, wherein the CAD module is further to generate a DICOM CAD SR object.

30. The system of claim 29, wherein the CAD module is further to send the DICOM CAD SR object to the network.

31. The system of claim 29, wherein the DICOM CAD SR object is used by the display to display the annotation map.

* * * * *